(12) United States Patent
Li et al.

(10) Patent No.: US 7,262,183 B2
(45) Date of Patent: Aug. 28, 2007

(54) SUBSTITUTED 5-MEMBERED N-HETEROCYCLIC COMPOUNDS AND THEIR USES FOR TREATING OR PREVENTING NEURODEGENERATIVE DISEASES

(75) Inventors: Song Li, Beijing (CN); Liqin Zhao, Beijing (CN); Lili Wang, Beijing (CN); Beifen Shen, Beijing (CN); Liuhong Yun, Beijing (CN)

(73) Assignees: Instititute of Pharmacology and Toxicology, Beijing (CN); Academy of Military Medical Sciences P.L.A. (CN)

( * ) Notice: Subject to any disclaimer, the term of this patent is extended or adjusted under 35 U.S.C. 154(b) by 98 days.

(21) Appl. No.: 10/498,104

(22) PCT Filed: Dec. 5, 2002

(86) PCT No.: PCT/CN02/00870

§ 371 (c)(1),
(2), (4) Date: Mar. 29, 2005

(87) PCT Pub. No.: WO03/048150

PCT Pub. Date: Jun. 12, 2003

(65) Prior Publication Data

US 2005/0171166 A1    Aug. 4, 2005

(30) Foreign Application Priority Data

Dec. 6, 2001  (CN) .................................. 01142743

(51) Int. Cl.
*A61K 31/426* (2006.01)
*A61K 31/4439* (2006.01)
*C07D 277/06* (2006.01)
*C07D 417/12* (2006.01)

(52) U.S. Cl. ................... 514/201; 514/342; 546/269.7; 548/201

(58) Field of Classification Search ................ 548/201; 546/269.7; 514/342, 365
See application file for complete search history.

(56) References Cited

U.S. PATENT DOCUMENTS 6,274,602 B1 * 8/2001 Steiner et al. .............. 514/330

6,274,617 B1 * 8/2001 Steiner et al. .............. 514/423

FOREIGN PATENT DOCUMENTS

| WO | WO96/40633 | 12/1996 |
| WO | WO96/41609 | 12/1996 |
| WO | WO98/13355 | 4/1998 |
| WO | WO9962487 A1 * | 12/1999 |
| WO | WO 00/09108 | 2/2000 |
| WO | WO 00/16603 | 3/2000 |
| WO | WO 01/38304 A1 | 5/2001 |
| WO | WO 2003028734 A1 * | 4/2003 |

OTHER PUBLICATIONS

Poisel et al. Chemische Berichte (1973), 106(10), 3408-20. ** CAS Abstract attached.*
Henery-Logan et al. Tetrahedron Letters, 1973, 13, 1103-4. *CAS Abstract provided.*
Johnansson et al. Acta Chemica Scandinavia, Series B: Organic Chemistry and Biochemistry, 1976, B30(5), 383-90. *CAS Abstract provided.*
Dunkerton et al. Tetrahedron Letters 1980, 21(19), 1803-6 *CAS Abstract provided.*

* cited by examiner

*Primary Examiner*—Kamal A. Saeed
*Assistant Examiner*—Jason M. Nolan
(74) *Attorney, Agent, or Firm*—Edwards Angell Palmer & Dodge LLP; David G. Conlin; Mark D. Russett

(57) ABSTRACT

This invention relates to substituted 5-membered N-Herterocyclic neurotrophic compounds of formula (I) or pharmaceutically acceptable salts or hydrates thereof, wherein $R_1$, $R_2$, $R_3$, $R_4$, V, W, X, Y, and Z are as defined in the description; their preparation methods, compositions comprising the same, and their use as inhibitors of FK560 binding proteases (FKBPs) activity for treating and preventing neurodegenerative diseases and other nerve disorders associated with nerve injuries or other related diseases.

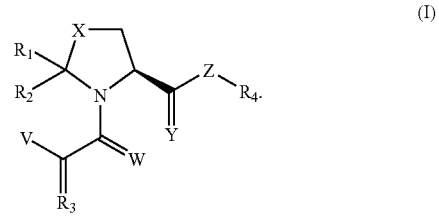

(I)

3 Claims, 2 Drawing Sheets

Figure 1:

SUBSTITUTED 5-MEMBERED N-HETEROCYCLIC COMPOUNDS AND THEIR USES FOR TREATING OR PREVENTING NEURODEGENERATIVE DISEASES

This application is a PCT application, PCT/CN02/00870, which was filed on Dec. 5, 2002, and claims the priority date of Dec. 6, 2001 in P. R. China.

FIELD OF THE INVENTION

This invention relates to substituted 5-membered N-Herterocyclic neurotrophic compounds, their preparation methods, compositions comprising the same, and their use as inhibitors of FK560 binding proteins (FKBPs) enzyme activity for treating and preventing neurodegenerative diseases and other nerve disorders associated with nerve injury or other related diseases.

BACKGROUND OF THE RELATED ART

Neurodegenerative disease is a kind of progressive disease associated with age including, for example, Alzheimer's disease, Parkinson's disease, Huntington's disease and amyotrophic lateral sclerosis (ALS). At present there are no effective methods for treating this kind of disease due to its unclear mechanism and complicated invasion cause.

As very important biological active molecules existed in the nerve system, neurotrophic factors (NTFs), such as nerve growth factor (NGF), brain derived growth factor (BDGF), glial derived growth factor (GDGF) and neurotropin-3 (NT-3), can effectively promote regeneration and functional recovery of injured neuraxon[1]. So, neurotrophic factors are considered as a potential drug for treating neurodegenerative diseases. However, effective clinical application of such neurotrophic molecules is restricted due to the insurmountable low bioavailability and specificity of large protein molecules.

In addition to the immunity system, FKBPs have been found to be present at high concentrations in the central nervous system[2]. It has been found that the immunosuppressant FK506[3], as a potent inhibitor of FKBPs, can remarkably promote the neurite outgrowth and the nerve fiber differentiation, and show excellent blood-brain barrier penetrability and bioavailability[4]. However, when administered chronically, the immunosuppressant FK506 induces a number of potential side and toxic actions, including nephrotoxicity[6], such as impairment of glomerular filtration[5] and irreversible interstitial fibrosis; and neurological deficits, such as involuntary tremors and non-specific cerebral angina[7].

OBJECT OF THE INVENTION

The object of the present invention is to provide non-immunosuppressive small molecule compounds acting on FKBPs for promoting the nerve outgrowth and regeneration in various neuropathological situations including neurological diseases associated with neurodegeneration, such as Alzheimer's disease, Parkinson's disease and amyotrophic lateral sclerosis, and neurological disorders caused by various physical injuries (such as mechanical injuries or concussions) or other diseases (such as diabetes or autoimmune acquired diseases).

BRIEF DESCRIPTION OF THE INVENTION

It has been found that the compound of formula (I) may be used as FKBPs for promoting the nerve outgrowth and regeneration in various neuropathological situations. Thus, the compound of formula (I) could be used to prevent and/or treat neurological diseases associated with neurodegeneration.

In the first aspect, the present invention relates to a compound of formula (I):

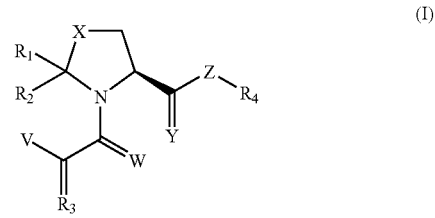

or a pharmaceutically acceptable salt or a hydrate thereof, wherein:

X is $CH_2$, O, S, SO, $SO_2$ or $NR_5$, wherein $R_5$ is hydrogen or $C_1$-$C_4$ alkyl;

Y is O or S;

Z is $CH_2$, O or $NR_6$, wherein $R_6$ is hydrogen or $C_1$-$C_6$ alkyl;

V and W are independently selected from a group consisting of $CH_2$, O, S, and $NR_7$, wherein $R_7$ is hydrogen or methyl, and V and W in one compound are same or different;

$R_1$ and $R_2$ are independently selected from a group consisting of hydrogen, $C_1$-$C_3$ alkyl and $C_2$-$C_3$ alkenyl, and $R_1$ and $R_2$ in one compound are same or different, but at least one of these two groups must be a non-hydrogen group;

$R_3$ is straight or branched chain $C_1$-$C_8$ alkyl, straight or branched chain $C_2$-$C_8$ alkenyl, $C_3$-$C_8$ cycloalkyl, $C_5$-$C_7$ cycloalkenyl, or $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$;

$R_4$ is straight or branched chain $C_1$-$C_{10}$ alkyl or straight or branched chain $C_2$-$C_{10}$ alkenyl, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;

$Ar_1$ and $Ar_2$ are independently selected from mono-, di-, or tricyclic aromatic carbocyclic ring and heterocyclic ring containing 1 to 6 heteroatoms selected from a group consisting of O, S and N, wherein each single ring is 5-membered or 6-membered, and said ring may be unsubstituted or substituted in one to five position(s) with 1 to 3 following groups: halogens, nitro, hydroxy, hydroxymethyl, trifluoromethyl, trifluoromethoxyl, straight or branched chain $C_1$-$C_6$ alkyl, straight or branched chain $C_2$-$C_6$ alkenyl, $C_1$-$C_4$ alkoxy, $C_2$-$C_4$ alkenoxy, phenoxy, benzyloxy, carboxyl or amino.

In another aspect, the present invention relates to a pharmaceutical composition comprising at least one compound of formula (I) or a pharmaceutically acceptable salt or a solvate thereof, and pharmaceutically acceptable carriers or excipients.

In a further aspect, the present invention relates to the a method of preparing a compound of formula (I) or a pharmaceutically acceptable salt or a solvate thereof, comprising:

(i) reacting compound 1 with dry acetone to obtain compound 2,

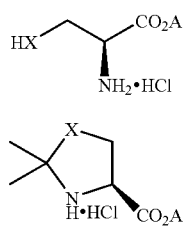

(ii) reacting compound 2 with methyl or ethyl oxalyl chloride to obtain compound 3,

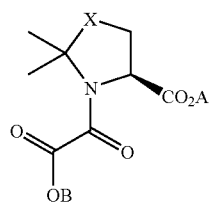

(iii) reacting compound 3 with alkyl Grignard reagent $R_3MgY$ to obtain compound 4,

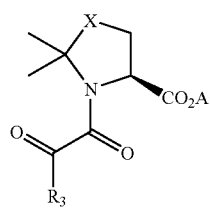

(iv) reacting compound 4 with LiOH to obtain compound 5, and

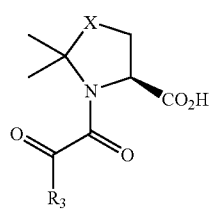

(v) reacting compound 5 with $R_4OH$ to obtain the compound of formula (I).

If desired, the obtained compound of formula (I) can be converted to a pharmaceutically acceptable salt using a suitable acid or base.

In a still further aspect, the present invention relates to the use of at least one compound of formula (I) or a pharmaceutically acceptable salt or a hydrate thereof in preparing a drug for treating and/or preventing diseases associated with nerve pathological changes.

The present invention also relates to a method for preventing and/or treating diseases associated with nerve pathological changes comprising administering a therapeutically effective amount of a compound of formula (I) or a pharmaceutically acceptable salt or a hydrate thereof to the patients in need.

DETAILED DESCRIPTION OF THE INVENTION

The present invention relates to a compound of formula (I):

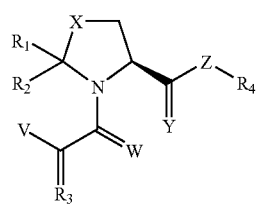

or a pharmaceutically acceptable salt or a hydrate thereof, wherein:

X is $CH_2$, O, S, SO, $SO_2$ or $NR_5$, wherein $R_5$ is hydrogen or $C_1$-$C_4$ alkyl;

Y is O or S;

Z is $CH_2$, O or $NR_6$, wherein $R_6$ is hydrogen or $C_1$-$C_6$ alkyl;

V and W are independently selected from a group consisting of $CH_2$, O, S, and $NR_7$, wherein $R_7$ is hydrogen or methyl, and V and W in one compound are same or different;

$R_1$ and $R_2$ are independently selected from a group consisting of hydrogen, $C_1$-$C_3$ alkyl and $C_2$-$C_3$ alkenyl, and $R_1$ and $R_2$ in one compound are same or different, but at least one of these two groups must be a non-hydrogen group;

$R_3$ is straight or branched chain $C_1$-$C_8$ alkyl, straight or branched chain $C_2$-$C_8$ alkenyl, $C_3$-$C_8$ cycloalkyl, $C_5$-$C_7$ cycloalkenyl, or $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$;

$R_4$ is straight or branched chain $C_1$-$C_{10}$ alkyl or straight or branched chain $C_2$-$C_{10}$ alkenyl, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;

$Ar_1$ and $Ar_2$ are independently selected from mono-, di-, or tricyclic aromatic carbocyclic ring and heterocyclic ring containing 1 to 6 heteroatoms selected from a group consisting of O, S and N, wherein each single ring is 5-membered or 6-membered, and said ring may be unsubstituted or substituted in one to five position(s) with 1 to 3 following groups: halogens, nitro, hydroxy, hydroxymethyl, trifluoromethyl, trifluoromethoxyl, straight or branched chain $C_1$-$C_6$ alkyl, straight or branched chain $C_2$-$C_6$ alkenyl, $C_1$-$C_4$ alkoxy, $C_2$-$C_4$ alkenoxy, phenoxy, benzyloxy, carboxyl or amino.

According to the present invention, one preferred embodiment is the compound of formula (I) represented by the compound of formula (II):

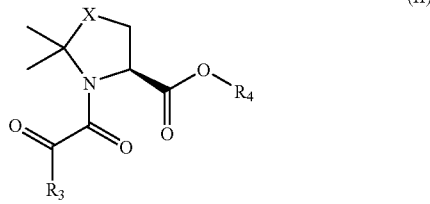

(II)

or a pharmaceutically acceptable salt or a hydrate thereof, wherein:

X is $CH_2$, O, S, SO, $SO_2$ or $NR_5$, wherein $R_5$ is hydrogen, methyl or ethyl;

$R_3$ is straight or branched chain $C_1$-$C_8$ alkyl, straight or branched chain $C_2$-$C_8$ alkenyl, $C_3$-$C_8$ cycloalkyl, $C_5$-$C_7$ cycloalkenyl, or $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$;

$R_4$ is straight or branched chain $C_1$-$C_{10}$ alkyl or straight or branched chain $C_2$-$C_{10}$ alkenyl, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;

$Ar_1$ and $Ar_2$ are independently selected from mono-, di-, or tricyclic aromatic carbocyclic ring and heterocyclic ring containing 1 to 6 heteroatoms selected from a group consisting of O, S and N, wherein each single ring is 5-membered or 6-membered, and said ring may be unsubstituted or substituted in one to five position(s) with 1 to 3 following groups: halogens, nitro, hydroxy, hydroxymethyl, trifluoromethyl, trifluoromethoxyl, straight or branched chain $C_1$-$C_6$ alkyl, straight or branched chain $C_2$-$C_6$ alkenyl, $C_1$-$C_4$ alkoxy, $C_2$-$C_4$ alkenoxy, phenoxy, benzyloxy, carboxyl or amino.

According to the present invention, another preferred embodiment is the compound of formula (I) represented by the compound of formula (II) or a pharmaceutically acceptable salt or a hydrate thereof, wherein:

X is O or S;

$R_3$ is straight or branched chain $C_1$-$C_8$ alkyl, straight or branched chain $C_2$-$C_8$ alkenyl, $C_3$-$C_8$ cycloalkyl, $C_5$-$C_7$ cycloalkenyl, or $Ar_1$, wherein alkyl or alkenyl chain may be unsubstituted or substituted with one or more of the following groups: $C_3$-$C_8$ cycloalkyl, $C_5$-$C_7$ cycloalkenyl, or $Ar_2$;

$R_4$ is straight or branched chain $C_1$-$C_{10}$ alkyl or straight or branched chain $C_2$-$C_{10}$ alkenyl, wherein alkyl or alkenyl chain may be unsubstituted or substituted with one or more of the following groups: $C_3$-$C_8$ cycloalkyl, $C_5$-$C_7$ cycloalkenyl, or $Ar_2$, in addition, wherein a part of carbon atoms of alkyl or alkenyl can be replaced by nitrogen or oxygen atoms;

$Ar_1$ and $Ar_2$ are independently selected from phenyl, biphenyl, 1-naphthyl, 2-naphthyl, 2-furyl, 3-furyl, 2-thienyl, 3-thienyl, 2-pyridyl, 3-pyridyl, 4-pyridyl, 2-thiazolyl, 2-indolyl, and 3-indolyl, and each $Ar_1$ or $Ar_2$ is substituted with 1 to 3 following groups: halogens, nitro, hydroxy, hydroxymethyl, trifluoromethyl, trifluoromethoxyl, straight or branched chain $C_1$-$C_6$ alkyl, straight or branched chain $C_2$-$C_6$ alkenyl, $C_1$-$C_4$ alkoxy, $C_2$-$C_4$ alkenoxy, phenoxy, benzyloxy, carboxyl or amino.

Preferred Compounds of the Invention Include:

3-(3-pyridyl)-1-propyl (2S)-5,5-dimethyl-1-(2-cyclohexyl-1,2-dioxoethyl)-2-(4-thiazolidine)carboxylate, 3-phenyl-1-propyl (2S)-5,5-dimethyl-1-(2-cyclohexyl-1,2-dioxoethyl)-2-(4-thiazolidine)carboxylate, (E)-3-phenyl-prop-2-en-1-yl (2S)-5,5-dimethyl-1-(2-cyclohexyl-1,2-dioxoethyl)-2-(4-thiazolidine)carboxylate, 3-phenoxy-1-propyl (2S)-5,5-dimethyl-1-(2-cyclohexyl-1,2-dioxoethyl)-2-(4-thiazolidine)carboxylate, 2-[N-ethyl-N-(3-methylphenyl)]amino-1-ethyl (2S)-5,5-dimethyl-1-(2-cyclohexyl-1,2-dioxoethyl)-2-(4-thiazolidine)carboxylate, 2-(2-thienyl)-1-ethyl (2S)-5,5-dimethyl-1-(2-cyclohexyl-1,2-dioxoethyl)-2-(4-thiazolidine)carboxylate, dec-9-en-1-yl (2S)-5,5-dimethyl-1-(2-cyclohexyl-1,2-dioxoethyl)-2-(4-thiazolidine)carboxylate, 3-(3-pyridyl)-1-propyl (2S)-5,5-dimethyl-1-(2-cyclopentyl-1,2-dioxoethyl)-2-(4-thiazolidine)carboxylate, 3-(3-pyridyl)-1-propyl (2S)-5,5-dimethyl-1-(3,3-dimethyl-1,2-dioxopentyl)-2-(4-thiazolidine)carboxylate, 3-phenyl-1-propyl (2S)-5,5-dimethyl-1-(3,3-dimethyl-1,2-dioxopentyl)-2-(4-thiazolidine)carboxylate, (E)-3-phenyl-prop-2-en-1-yl (2S)-5,5-dimethyl-1-(3,3-dimethyl-1,2-dioxopentyl)-2-(4-thiazolidine)carboxylate, 3-phenoxy-1-propyl (2S)-5,5-dimethyl-1-(3,3-dimethyl-1,2-dioxopentyl)-2-(4-thiazolidine)carboxylate, 2-[N-ethyl-N-(3-methylphenyl)]amino-1-ethyl (2S)-5,5-dimethyl-1-(3,3-dimethyl-1,2-dioxopentyl)-2-(4-thiazolidine)carboxylate, 2-(2-thienyl)-1-ethyl (2S)-5,5-dimethyl-1-(3,3-dimethyl-1,2-dioxopentyl)-2-(4-thiazolidine)carboxylate, 3-(3-pyridyl)-1-propyl (2S)-5,5-dimethyl-1-(3,3-dimethyl-1,2-dioxobutyl)-2-(4-thiazolidine)carboxylate, 3-(6-methyl-2-pyridyl)-1-propyl (2S)-5,5-dimethyl-1-(3,3-dimethyl-1,2-dioxobutyl)-2-(4-thiazolidine)carboxylate, 3-phenyl-1-propyl (2S)-5,5-dimethyl-1-(3,3-dimethyl-1,2-dioxobutyl)-2-(4-thiazolidine)carboxylate, (E)-3-phenyl-prop-2-en-1-yl (2S)-5,5-dimethyl-1-(3,3-dimethyl-1,2-dioxobutyl)-2-(4-thiazolidine)carboxylate, 1-phenoxy-2-propyl (2S)-5,5-dimethyl-1-(3,3-dimethyl-1,2-dioxobutyl)-2-(4-thiazolidine)carboxylate, 3-cyclohexyl-1-propyl (2S)-5,5-dimethyl-1-(3,3-dimethyl-1,2-dioxobutyl)-2-(4-thiazolidine)carboxylate, (1R)-1-(4-methoxyphenyl)-3-phenyl-1-propyl (2S)-5,5-dimethyl-1-(3,3-dimethyl-1,2-dioxobutyl)-2-(4-thiazolidine)carboxylate, 3-(N,N-dibenzylamino)-1-propyl (2S)-5,5-dimethyl-1-(3,3-dimethyl-1,2-dioxobutyl)-2-(4-thiazolidine)carboxylate, dec-9-en-1-yl (2S)-5,5-dimethyl-1-(3,3-dimethyl-1,2-dioxobutyl)-2-(4-thiazolidine)carboxylate, (2R)-1-methoxy-2-propyl (2S)-5,5-dimethyl-1-(3,3-dimethyl-1,2-dioxobutyl)-2-(4-thiazolidine)carboxylate, 3-(3-pyridyl)-1-propyl (2S)-5,5-dimethyl-1-(1,2-dioxooctyl)-2-(4-thiazolidine)carboxylate, 3-(6-methyl-2-pyridyl)-1-propyl (2S)-5,5-dimethyl-1-(1,2-dioxooctyl)-2-(4-thiazolidine)carboxylate, 3-phenyl-1-propyl(2S)-5,5-dimethyl-1-(1,2-dioxooctyl)-2-(4-thiazolidine)carboxylate, (E)-3-phenyl-prop-2-en-1-yl (2S)-5,5-dimethyl-1-(1,2-dioxooctyl)-2-(4-thiazolidine)carboxylate, 2-(2-chlorophenyl)-1-ethyl (2S)-5,5-dimethyl-1-(1,2-dioxooctyl)-2-(4-thiazolidine)carboxylate, 3-(3-pyridyl)-1-propyl (2S)-5,5-dimethyl-1-(1,2-dioxodecyl)-2-(4-thiazolidine)carboxylate, 3-(6-methyl-2-pyridyl)-1-propyl (2S)-5,5-dimethyl-1-(1,2-dioxodecyl)-2-(4-thiazolidine)carboxylate,
2-(2-chlorophenyl)-1-ethyl (2S)-5,5-dimethyl-1-(1,2-dioxodecyl)-2-(4-thiazolidine)carboxylate,
(2R)-1-methoxy-2-propyl (2S)-5,5-dimethyl-1-(1,2-dioxodecyl)-2-(4-thiazolidine)carboxylate,
2-pentyl(2S)-5,5-dimethyl-1-(1,2-dioxodecyl)-2-(4-thiazolidine)carboxylate,
3-(3-pyridyl)-1-propyl (2S)-5,5-dimethyl-1-(1,2-dioxo-2-phenyl)ethyl-2-(4-thiazolidine)carboxylate,
3-phenyl-1-propyl (2S)-5,5-dimethyl-1-(1,2-dioxo-2-phenyl)ethyl-2-(4-thiazolidine)carboxylate,
(E)-3-phenyl-prop-2-en-1-yl (2S)-5,5-dimethyl-1-(1,2-dioxo-2-phenyl)ethyl-2-(4-thiazolidine)carboxylate,
3-cyclohexyl-1-propyl (2S)-5,5-dimethyl-1-(1,2-dioxo-2-phenyl)ethyl-2-(4-thiazolidine)carboxylate,
dec-9-en-1-yl (2S)-5,5-dimethyl-1-(1,2-dioxo-2-phenyl)ethyl-2-(4-thiazolidine)carboxylate,
3-(3-pyridyl)-1-propyl (2S)-5,5-dimethyl-1-[2-(4-chlorophenyl)-1,2-dioxoethyl]-2-(4-thiazolidine)carboxylate,
3-(3-pyridyl)-1-propyl (2S)-5,5-dimethyl-1-[1,2-dioxo-2-(2,4,6-trimethylphenyl)]ethyl-2-(4-thiazolidine)carboxylate,
3-phenyl-1-propyl (2S)-5,5-dimethyl-1-[1,2-dioxo-2-(2,4,6-trimethylphenyl)]ethyl-2-(4-thiazolidine)carboxylate,
(E)-3-phenyl-prop-2-en-1-yl (2S)-5,5-dimethyl-1-[1,2-dioxo-2-(2,4,6-trimethylphenyl)]ethyl-2-(4-thiazolidine)carboxylate,
3-cyclohexyl-1-propyl (2S)-5,5-dimethyl-1-[1,2-dioxo-2-(2,4,6-trimethylphenyl)]ethyl-2-(4-thiazolidine)carboxylate,
3-phenoxy-1-propyl (2S)-5,5-dimethyl-1-[1,2-dioxo-2-(2,4,6-trimethylphenyl)]ethyl-2-(4-thiazolidine)carboxylate,
2-(2-thienyl)-1-ethyl (2S)-5,5-dimethyl-1-[1,2-dioxo-2-(2,4,6-trimethylphenyl)]ethyl-2-(4-thiazolidine)carboxylate,
2-aminobenzyl (2S)-5,5-dimethyl-1-[1,2-dioxo-2-(2,4,6-trimethylphenyl)]ethyl-2-(4-thiazolidine)carboxylate,
2-(N-benzyl-N-methyl)amino-1-ethyl (2S)-5,5-dimethyl-1-[1,2-dioxo-2-(2,4,6-trimethylphenyl)]ethyl-2-(4-thiazolidine)carboxylate,
1-phenoxy-2-propyl (2S)-5,5-dimethyl-1-[1,2-dioxo-2-(2,4,6-trimethylphenyl)]ethyl-2-(4-thiazolidine)carboxylate,
dec-9-en-1-yl (2S)-5,5-dimethyl-1-[1,2-dioxo-2-(2,4,6-trimethylphenyl)]ethyl-2-(4-thiazolidine)carboxylate,
3-(3-pyridyl)-1-propyl (2S)-5,5-dimethyl-1-(1,2-dioxo4-methyl-4-phenyl)pentyl-2-(4-thiazolidine)carboxylate,
2-phenylbenzyl (2S)-5,5-dimethyl-1-(1,2-dioxo4-methyl-4-phenyl)pentyl-2-(4-thiazolidine)carboxylate,
3-(3-pyridyl)-1-propyl (2S)-5,5-dimethyl-1-(3,3-dimethyl-1,2-dioxopentyl)-2-(4-oxazolidine)carboxylate, and
3-phenyl-1-propyl (2S)-5,5-dimethyl-1-(3,3-dimethyl-1,2-dioxopentyl)-2-(4-oxazolidine)carboxylate.

The compounds of the present invention can be used in the form of salts derived from inorganic or organic acids or inorganic or organic bases. Such acid salts include, but are not limited to, the following salts: hydrochloride, hydrobromide, hydriodide, nitrate, sulfate, bisulfate, phosphate, hydrophosphate, acetate, propionate, butanoate, oxalate, trimethyl acetate, adipate, alginate, lactate, citrate, tartrate, succinate, maleate, fumarate, picrate, aspartate, gluconate, benzoate, methanesulfonate, ethanesulfonate, benzenesulfonate, tosylate and dihydroxynaphthoate. Such base salts include, but are not limited to, the following salts: ammonium salts, alkali metal salts such as sodium and potassium salts, alkaline earth metal salts such as calcium and magnesium salts, salts derived from organic bases such as dicyclohexylamine and N-methyl-D-glucamine salts, and salts derived from amino acids such as arginine and lysine salts.

The compounds of the present invention can be synthesized through the following route.

Scheme I:

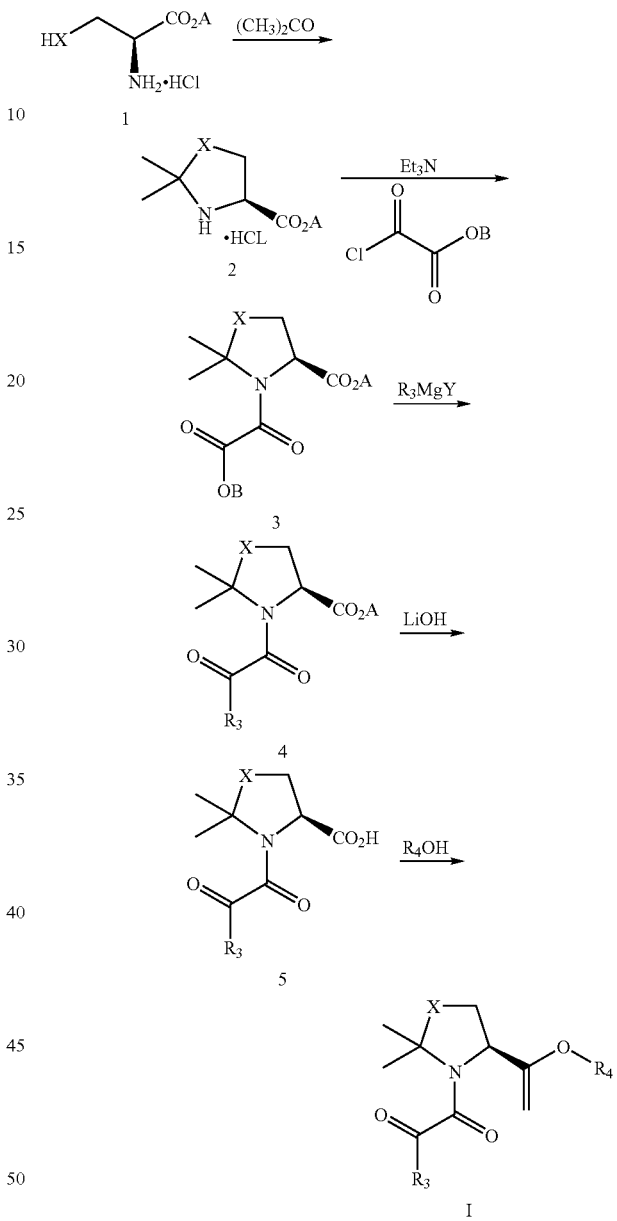

wherein: X is O or S; Y is Cl, Br or I; A is $CH_3$ or $C_2H_5$; and B is $CH_3$ or $C_2H_5$.

In the methods of preparing these compounds, intermediate compound 2 was prepared according to the method described in the references 8 and 9. Under the condition of reflux, the methyl ester or ethyl ester of corresponding optically active amino acid reacted with dry acetone to obtain compound 2. Compound 2 reacted with methyl or ethyl oxalyl chloride in the presence of triethyl amine in a suitable organic solvent (e.g. anhydrous ether) at 0° C. to obtain compound 3. Without further purification, compound 3 reacted with allyl Grignard reagent in THF (or ether) at low temperature (−70 to −80° C., preferably −78° C.) to obtain intermediate compound 4. Compound 4 was purified by column chromatograph where the silica gel used was a routine silica gel for chromatography (particle size: 10-40μ), and the eluant was selected from a single solvent or mixed solvents (preferably ethyl acetate and petroleum ether (60-90° C.)). Compound 4 underwent catalytic hydrolysis by using aqueous LiOH solution (preferably 1N) in a suitable alcohol (preferably methanol) at room temperature and then was acidified with diluent hydrogen chloride (preferably 1N) to obtain intermediate compound 5. Without further purification, compound 5 underwent esterification with $R_4OH$ in a suitable solvent (e.g. $CH_2Cl_2$) catalyzed by a small amount of dicyclohexylcarbodiimide, camphorsulphonic acid and 4,4-dimethylaminopyridine under a nitrogen atmosphere to obtain the preferred compound of formula (I) of the present invention.

According to the present invention, the pharmaceutical composition includes an effective amount of a compound of formula (I) or a pharmaceutical salt or a hydrate thereof, and one or more suitable pharmaceutically acceptable carriers. The pharmaceutically acceptable carrier is selected from, but is not limited to, the following carriers: ion exchanger, aluminum oxide, aluminum stearate, lecithin, serum protein (e.g. human serum protein), buffer substance (e.g. phosphate), glycerol, sorbic acid, potassium sorbate, mixture of partial glycerides of saturated vegetable fatty acids, water, salt or electrolyte (e.g. protamine sulfate, disodium hydrogen phosphate, potassium hydrogen phosphate, sodium chloride, zinc salt), colloidal silicon oxide, magnesium trisilicate, polyvinylpyrrolidone, cellulose, polyethylene glycol, sodium carboxymethycellulose, polyacrylate, beeswax, polyethylene-polyoxopropylene block polymer and lanolin.

The compound of the present invention is a kind of potent neuroregulation molecules having an affinity for FKBPs. In contrast to FK506, the compound of the present invention does not result in immunosuppression. The neuroregulation activity comprises, but is not limited to, repair of damaged neurons, promotion of neuronal regeneration, prevention of neurodegeneration and treatment of neurological disorders associated with neurodegeneration or peripheral nerve pathological changes. The neurological disorders that may be treated include, but are not limited to, Alzheimer's disease, Parkinson's disease, Huntington's disease and amyotrophic lateral sclerosis, nerve pathological changes associated with acquired immunodeficiency, cerebrospinal multiple sclerosis, apoplexy or brain injury associated with physical stimulation, various neurodegenerative diseases affecting central or nervous system, cerebellum-brain stem atrophy, progressive ataxia syndrome, muscular dystrophy, progressive muscular atrophy, progressive bulbar inherited muscular atrophy, physical or traumatic injury of central or peripheral nervous system, prolapsed intervertebral disk syndrome, cervical spondylosis, thoracic outlet destruction syndromes, nerve plexus disorders, thoracic brachial plexus syndrome, various peripheral nerve pathological changes, trigeminal neuralgia, glossopharyngeal neuralgia, facial paralysis, various autoimmune disease which may cause injury of central or peripheral nervous system, myasthenia gravis, Guillain-Barre syndrome, dapsone ticks, bulbar and postbulbar optic nerve pathological changes, retinopathy, postbulbar optic neuritis, audition disorders, or tinnitus.

Among other things, the preferred neurological disorders include, but are not limited to, neurological disorders associated with neurodegeneration such as Alzheimer's disease, Parkinson's disease and amyotrophic lateral sclerosis, and neurological disorders associated with peripheral nerve pathological changes, which usually are caused by physical injuries brain or spinal cord or other associated diseases.

According to the invention, the compound of the present invention may be administered orally, by inhalation spray, rectally, nasally, buccally, vaginally, topically, parenterally (such as, subcutaneous, intravenous, intramuscular, intraperitoneal, intrachecal, intraventricular, intrasteral, and intracranial injection or infusion techniques), or via an implanted reservoir, preferably orally, intraperitoneally, or intravenously. In addition, in order to treat central nervous system disorders effectively, the compound of the present invention is preferably administered intraventricularly to overcome possible low blood-brain barrier penetration of the compound.

When administered orally, the compound of the invention may be produced in any orally acceptable formulation forms comprising, but being not limited to, tablets, capsules, aqueous solutions or aqueous suspensions. Typically, the carriers used for tablets comprises lactose and corn starch. In addition, lubricating agents such as magnesium stearate may also be added. Usually, the diluents used for capsules comprise lactose and dried corn starch. Aqueous suspension formulations generally comprise mixture of suitable emulsifying and suspending agents with the active ingredient. If desired, the oral formulation forms may further comprise sweetening agents, flavoring agents or coloring agents.

The compounds of the invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. The compounds of the invention may be prepared into different topical administration formulations in accordance with the areas or organs.

For topical application to eyes, the compounds of the invention can be formulated as micronized suspensions or solutions in isotonic, pH adjusted sterile saline, either with or without a preservative such as benzylalkonium chloride. Alternatively, for the ophthalmic uses, the compounds may be formulated in an ointment such as petrolatum.

For topical application to the skin, the compounds can be formulated in a suitable ointment, lotion or cream wherein the active ingredient suspends or dissolves in one or more carriers. For example, the carriers suitable for ointment comprise mineral oil, liquid petrolatum, white petrolatum, propylene glycol, polyoxyethylene, polyoxypropylene, emulsifying wax and water; and the carriers suitable for lotion or cream comprise mineral oil, sorbitan monostearate, Tween 60, cetyl ester wax, cetearyl alcohol, 2-octyldodecanol, benzyl alcohol and water.

Topical application for the lower intestinal tract can be effected in a rectal suppository formulation (see above) or in a suitable enema formulation.

The compounds of the present invention may be administered in the form of sterile injectable preparations, for example, as sterile injectable aqueous or oleaginous suspensions. Among the acceptable carriers and solvents that may be employed are water, Ringer's solution and isotonic sodium chloride solution. In addition, sterile, fixed oils, such as mono- or di-glycerides, can be also employed as solvents or suspending mediums.

The compounds can be administered together with other neurotrophic substances such as neurotrophic growth factor (NGF), insulin growth factor (IGF-1), and derived growth factor thereof (gIGF-1), brain derived growth factor (BDGF), glial derived growth factor (GDGF), platelet derived growth factor (PDGF), fibroblast growth factor (aFGF and bFGF), ciliary neurotrophic factor (CNTF), neurotropin-3 (NT-3), and neurotropin-4/5 (NT-4/5), preferably NGF. Such two active ingredients may stimulate the growth of nerve synergistically.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration. Dosage levels on the order of about 0.01 mg to about 100 mg of the active ingredient/kg body weight/day are preferred.

EXAMPLES

The following examples are preferred illustrative examples of the invention and these preferred examples do not intend to limit the present invention.

Melting points were determined with a RY-1 melting point apparatus and the temperatures are not rectified. $^1$H NMR spectra were recorded on a Bruker ARX 400 spectrometer or on a US Varian Unity Inova 600 spectrometer. FAB mass spectra were recorded on a Zabspect high resolution magnetic mass spectrometer.

Example 1

Synthesis of 3-(3-pyridyl)-1-propyl (2S)-5,5-dimethyl-1-(2-cyclohexyl-1,2-dioxoethyl)-2-(4-thiazolidine)carboxylate 1.1 A suspension of L-cysteine ethyl ester hydrochloride (Acros) (10 g, 53.88 mmol) in dry acetone (150 mL) was refluxed under stirring for 1 hour. After cooled to room temperature, the white crystal solid was suction filtered and washed with ice cold acetone and collected to afford the product ethyl (2S)-5,5-dimethyl-2-(4-thiazolidine)carboxylate hydrochloride (9.75 g, 80.2%), mp 148-150° C.

1.2 A stirred suspension of ethyl (2S)-5,5-dimethyl-2-(4-thiazolidine)carboxylate hydrochloride (1.95 g, 8.64 mmol) in dry ethyl ether (30 mL) was cooled to 0° C., a solution of ethyl oxalyl chloride (1.77 g, 12.97 mmol) in dry ethyl ether (10 mL) together with a solution of triethylamine (1.83 g, 18.12 mmol) in dry ethyl ether (20 mL) were added dropwise separately at such a rate that the addition of these two solutions finished substantially at the same time. The resulting mixture was stirred at 0° C. for 1.5 h and then filtered to remove solids. The organic layer was washed with water, dried over MgSO$_4$, and concentrated to afford the product, ethyl (2S)-5,5-dimethyl-1-(1,2-dioxo-2-ethoxyethyl)-2-(4-thiazolidine)carboxylate (2.1 g, 84.1%) as a yellow oil, which was used in the next step without further purification.

1.3 A solution of ethyl (2S)-5,5-dimethyl-1-(1,2-dioxo-2-ethoxyethyi)-2-(4-thiazolidine)carboxylate (2.5 g, 8.65 mmol) in dry THF (75 mL) was cooled to about −80° C. and treated with a 2.0M solution of cyclohexyl magnesium chloride in ethyl ether (5.75 mL, 11.5 mmol). The resulting mixture was stirred at −80° C. for 5 hours and then poured into a saturated ammonium chloride solution (100 mL). After extracted with ethyl acetate, the organic layer was combined and washed with water, dried over MgSO$_4$ and concentrated. The crude product was purified by column chromatography on silica gel using ethyl acetate-petroleum ether (1:10) as the eluent to afford the product ethyl (2S)-5,5-dimethyl-1-(2-cyclohexyl-1,2-dioxoethyl)-2-(4-thiazolidine)carboxylate (2.2 g, 77.8%) as a yellow oil.

1.4 A mixture of ethyl (2S)-5,5-dimethyl-1-(2-cyclohexyl-1,2-dioxoethyl)-2-(4-thiazolidine)carboxylate (5.6 g, 17.13 mmol), 1N LiOH (31 mL) and methanol (100 mL) was stirred at 0° C. for 30 minutes and then stirred at room temperature overnight. The mixture was acidified with 1N HCl to pH 1, diluted with water, and extracted with ethyl acetate. The organic layer was washed with brine, dried over MgSO$_4$, and concentrated to afford the product (2S)-5,5-dimethyl-1-(2-cyclohexyl-1,2-dioxoethyl)-2-(4-thiazolidine)carboxylic acid (4.5 g, 87.9%) as a white powder, which was used in the next step without further purification.

1.5 A mixture of (2S)-5,5-dimethyl-1-(2-cyclohexy-1,2-dioxolethyl)-2-(4-thiazolidine)carboxylic acid (400 mg, 1.34 mmol), 3-(3-pyridyl)-1-propanol (275 mg, 2.01 mmol), dicyclohexylcarbodiimide (331 mg, 1.61 mmol), camphorsulphonic acid (94 mg, 0.41 mmoi) and 4-dimethylaminopyridine (50 mg, 0.41 mmol) in methylene chloride (20 mL) was stirred overnight under an nitrogen atmosphere. The reaction mixture was filtered and concentrated, the crude material was purified by column chromatography on silica gel using ethyl acetate-petroleum ether (3:1) as the eluent to afford the product 3-(3-pyridyl)-1-propyl (2S)-5,5-dimethyl-1-(2-cyclohexyl-1,2-dioxoethyl)-2-(4-thiazolidine)carboxylate (419 mg, 74.8%) as a colorless oil. MS [M+H]$^+$=419.2 m/e; $^1$H NMR (400 MHz, CDCl$_3$) □ 1.12-1.39 (m, 6H); 1.67-2.02 (m, 6H); 1.88 (s, 3H); 1.96 (s, 3H); 2.72 (t, 2H, J=7.8); 3.19 (m, 1H); 3.23 (dd, 1H, J=2.0, 12.3); 3.32 (dd, 1H, J=5.7, 12.3); 4.19 (m, 2H); 5.33 (dd, 1H, J=2.0, 5.7); 7.27 (m, 1H); 7.56 (d, 1H, J=7.9); 8.48 (s, 2H).

The following illustrative compounds of examples 2-52 can be prepared in the same manner as described in example 1 except using different R$_3$MgY and R$_4$OH.

Example 2

Synthesis of 3-phenyl-1-propyl (2S)-5,5-dimethyl-1-(2-cyclohexyl-1,2-dioxoethyl)-2-(4-thiazolidine)carboxylate The title compound was prepared in the same manner as described in example 1 wherein R$_3$MgY used is the same as that used in step 1.3 of example 1, and R$_4$OH used is 3-phenyl-1-propanol. MS [M+H]$^+$=418.1 m/e; $^1$H NMR (400 MHz, CDCl$_3$) □ 1.10-1.37 (m, 6H); 1.63-1.97 (m, 6H); 1.88 (s, 3H); 1.95 (s, 3H); 2.69 (t, 2H, J=7.4); 3.19 (m, 1H); 3.24 (dd, 1H, J=1.5, 12.4); 3.33 (dd, 1H, J=5.8, 12.4); 4.19 (m, 2H); 5.02 (dd, 1H, J=1.5, 5.8); 7.20 (m, 3H); 7.31 (m, 2H).

Example 3

Synthesis of (E)-3-phenyl-prop-2-en-1-yl (2S)-5,5-dimethyl-1-(2-cyclohexyl-1,2-dioxoethyl)-2-(4-thiazolidine)carboxylate The title compound was prepared in the same manner as described in example 1 wherein R$_3$MgY used is the same as that used in step 1.3 of example 1, and R$_4$OH used is (E)-3-phenyl-1-propen-2-ol. MS [M+H]⁺=416.2 m/e; ¹H NMR (400 MHz, CDCl₃) ☐ 1.09-1.37 (m, 6H); 1.61-1.95 (m, 6H); 1.88 (s, 3H); 1.95(s, 3H); 3.17 (m, 1H); 3.34 (m, 2H); 4.76 (ddd, 1H, J=1.2, 6.4, 12.7); 4.84 (ddd, 1H, J=1.2, 6.4, 12.7); 5.45 (dd, 1H, J=2.6, 5.2); 6.24 (dt, 1H, J=6.4, 15.9); 6.66 (d, 1H, J=15.9); 7.26-7.40 (m, 5H).

Example 4

Synthesis of 3-phenoxy-1-propyl (2S)-5,5-dimethyl-1-(2-cyclohexyl-1,2-dioxoethyl)-2-(4-thiazolidine)carboxylate The title compound was prepared in the same manner as described in example 1 wherein $R_3MgY$ used is the same as that used in step 1.3 of example 1, and $R_4OH$ used is 3-phenoxy-1-propyl. MS [M+H]⁺=434.1 m/e; ¹H NMR (400 MHz, CDCl₃) ☐ 1.11-1.38 (m, 6H); 1.64-1.95 (m, 4H); 1.86 (s, 3H); 1.93 (m, 3H); 2.14 (m, 2H); 3.16 (m, 1H); 3.29 (m, 2H); 4.04 (m, 2H); 4.38 (m, 2H); 5.34 (dd, 1H, J=3.0, 4.9); 6.88 (m, 2H); 6.95 (m, 1H); 7.28 (m, 2H).

Example 5

Synthesis of 2-[N-ethyl-N-(3-methylphenyl)]amino-1-ethyl (2S)-5,5-dimethyl-1-(2-cyclohexyl-1,2-dioxoethyl)-2-(4-thiazolidine)carboxylate The title compound was prepared in the same manner as described in example 1 wherein $R_3MgY$ used is the same as that used in step 1.3 of example 1, and $R_4OH$ used is 2-[N-ethyl-N-(3-methylphenyl)]amino-1-ethanol. MS [M+H]⁺=461.2 m/e; ¹H NMR (400 MHz, CDCl₃) ☐ 1.14-1.35 (m, 9H); 1.66-1.94 (m, 4H); 1.86 (s, 3H); 1.94 (s, 3H); 2.31 (s, 3H); 3.20 (m, 3H); 3.37 (m, 2H); 3.54 (m, 2H); 4.30 (m, 2H); 5.36 (m, 1H); 6.53 (m, 3H); 7.10 (m, 1H).

Example 6

Synthesis of 2-(2-thienyl)-1-ethyl (2S)-5,5-dimethyl-1-(2-cyclohexyl-1,2-dioxoethyl)-2-(4-thiazolidine)carboxylate The title compound was prepared in the same manner as described in example 1 wherein $R_3MgY$ used is the same as that used in step 1.3 of example 1, and $R_4OH$ used is 2-(2-thienyl)-1-ethanol. MS [M+H]⁺=410.1 m/e; ¹H NMR (400 MHz, CDCl₃) ☐ 1.15-1.36 (m, 6H); 1.66-1.96 (m, 4H); 1.86 (s, 3H); 1.91 (s, 3H); 3.16 (m, 3H); 3.27 (m, 2H); 4.38 (t, 2H, J=6.7); 5.36 (dd, 1H, J=2.6, 5.3); 6.85 (m, 1H); 6.94 (m, 1H); 7.17 (m, 1H).

Example 7

Syhthesis of dec-9-en-1-yl (2S)-5,5-dimethyl-1-(2-cyclohexyl-1,2-dioxoethyl)-2-(4-thiazolidine)carboxylate The title compound was prepared in the same manner as described in example 1 wherein $R_3MgY$ used is the same as that used in step 1.3 of example 1, and $R_4OH$ used is dec-9-en-1-ol. MS [M+H]⁺=438.2 m/e; ¹H NMR (400 MHz, CDCl₃) ☐ 1.08-2.12 (m, 25H); 1.83 (s, 3H); 1.87 (s, 3H); 3.16 (m, 2H); 4.16 (m, 2H); 4.93 (m, 1H); 4.99 (m, 1H); 5.37 (t, 1H, J=3.8); 5.80 (m, 1H).

Example 8

Synthesis of 3-(3-pyridyl)-1-propyl (2S)-5,5-dimethyl-1-(2-cyclopentyl-1,2-dioxoethyl)-2-(4-thiazolidine)carboxylate The title compound was prepared in the same manner as described in example 1 wherein $R_3MgY$ used is cyclopentyl magnesium chloride solution in ethyl ether (2.0M), and $R_4OH$ used is 3-(3-pyridyl)-1-propanol. MS [M+H]⁺=405.3 m/e; ¹H NMR (400 MHz, CDCl₃) ☐ 1.60-1.77 (m, 8H); 1.88 (s, 3H); 1.96 (s, 3H); 1.99 (m, 2H); 2.72 (t, 2H, J=8.0); 3.28 (dd, 1H, J=2.2, 12.3); 3.33 (dd, 1H, J=5.7, 12.3); 3.60 (m, 1H); 4.20 (m, 2H); 5.39 (dd, 1H, J=2.2, 5.7); 7.28 (m, 1H); 7.56 (d, 1H, J=7.8); 8.48 (s, 2H).

Example 9

Synthesis of 3-(3-pyridyl)-1-propyl (2S)-5,5-dimethyl-1-(3,3-dimethyl-1,2-dioxopentyl)-2-(4-thiazolidine)carboxylate The title compound was prepared in the same manner as described in example 1 wherein $R_3MgY$ used is 1,1-dimethyl-propyl magnesium chloride solution in ethyl ether (1.0M), and $R_4OH$ used is 3-(3-pyridyl)-1-propanol. MS [M+H]⁺=407.0 m/e; ¹H NMR (600 MHz, CDCl₃) ☐ 0.83 (t, 3H, J=7.2); 1.19 (s, 3H); 1.27 (s, 3H); 1.73 (q, 2H, J=7.2); 1.90 (s, 3H); 1.99 (s, 3H); 2.01 (m, 2H); 2.72 (t, 2H, J=7.8); 3.24 (d, 1H, J=12.0); 3.32 (dd, 1H, J=6.0, 12.0); 4.23 (m, 2H); 4.93 (d, 1H, J=6.0); 7.23 (m, 1H); 7.52 (d, 1H, J=7.2); 8.47 (s, 2H).

Example 10

Synthesis of 3-phenyl-1-propyl (2S)-5,5-dimethyl-1-(3,3-dimethyl-1,2-dioxopentyl)-2-(4-thiazolidine)carboxylate The title compound was prepared in the same manner as described in example 1 wherein $R_3MgY$ used is the same as that used in example 9, and $R_4OH$ used is 3-phenyl-1-propanol. MS [M+H]⁺=406.0 m/e; ¹H NMR (400 MHz, CDCl₃) ☐ 0.83 (t, 3H, J=7.5); 1.18 (s, 3H); 1.27 (s, 3H); 1.72 (m, 2H); 1.90 (s, 3H); 1.98 (s, 3H); 2.02 (m, 2H); 2.70 (t, 2H, J=7.6); 3.23 (dd, 1H, J=1.2, 12.2); 3.31 (dd, 1H, J=6.0, 12.2); 4.20 (m, 2H); 4.96 (dd, 1H, J=1.2, 6.0); 7.17-7.31 (m, 5H).

Example 11

Synthesis of (E)-3-phenyl-prop-2-en-1-yl (2S)-5,5-dimethyl-1-(3,3-dimethyl-1,2-dioxopentyl)-2-(4-thiazolidine)carboxylate The title compound was prepared in the same manner as described in example 1 wherein $R_3MgY$ used is the same as that used in example 9, and $R_4OH$ used is (E)-3-phenyl-prop-2-en-1-ol. MS [M+H]⁺=404.3 m/e; ¹H NMR (400 MHz, CDCl₃) ☐ 0.81 (t, 3H, J=7.5); 1.17 (s, 3H); 1.28 (s, 3H); 1.71 (m, 2H); 1.90 (s, 3H); 1.97 (s, 3H); 3.33 (m, 2H); 4.82 (m, 2H); 5.07 (dd, 1H, J=2.7, 4.6); 6.25 (dt, 1H, J=6.5, 15.9); 6.68 (d, 1H, J=15.9); 7.26-7.40 (m, 5H).

Example 12

Synthesis of 3-phenoxy-1-propyl (2S)-5,5-dimethyl-1-(3,3-dimethyl-1,2-dioxopentyl)-2-(4-thiazolidine)carboxylate The title compound was prepared in the same manner as described in example 1 wherein $R_3MgY$ used is the same as that used in example 9, and $R_4OH$ used is 3-phenoxy-1-propanol. MS [M+H]$^+$=422.1 m/e; $^1$H NMR (400 MHz, CDCl$_3$) ☐ 0.82 (t, 3H, J=7.5); 1.17 (s, 3H);1.26 (s, 3H); 1.71 (m, 2H); 1.88 (s, 3H); 1.95 (s, 3H); 2.15 (m, 2H); 3.24 (dd, 1H, J=1.4, 12.2); 3.30 (dd, 1H, J=5.8, 12.2); 4.05 (t, 2H, J=6.1); 4.40 (m, 2H); 4.93 (dd, 1H, J=1.4, 5.8); 6.90 (d, 2H, J=7.7); 6.95 (t, 1H, J=7.4); 7.30 (m, 2H).

Example 13

Synthesis of 2-[N-ethyl-N-(3-methylphenyl)]amino-1-ethyl (2S)-5,5-dimethyl-1-(3,3-dimethyl-1,2-dioxopentyl)-2-(4-thiazolidine)carboxylate The title compound was prepared in the same manner as described in example 1 wherein $R_3MgY$ used is the same as that used in example 9, and $R_4OH$ used is 2-[N-ethyl-N-(3-methylphenyl)]amino-1-ethanol. MS [M+H]$^+$=449.2 m/e; $^1$H NMR (400 MHz, CDCl$_3$) ☐ 0.82 (t, 3H, J=7.5); 1.13 (t, 3H, J=7.0); 1.18 (s, 3H); 1.28 (s, 3H); 1.73 (m, 2H); 1.88 (s, 3H); 1.96 (s, 3H); 2.31 (s, 3H); 3.16-3.18 (d, 1H, J=12.2); 3.27 (dd, 1H, J=5.9, 12.2); 3.38 (q, 2H, J=7.0); 3.56 (t, 2H, J=6.3); 4.31 (m, 2H); 4.98 (d, 1, J=5.9); 6.54 (m, 3H); 7.11 (m, 1H).

Example 14

Synthesis of 2-(2-thienyl)-1-ethyl (2S)-5,5-dimethyl-1-(3,3-dimethyl-1,2-dioxopentyl)-2-(4-thiazolidine)carboxylate The title compound was prepared in the same manner as described in example 1 wherein $R_3MgY$ used is the same as that used in example 9, and $R_4OH$ used is 2-(2-thienyl)-1-ethanol. MS [M+H]$^+$=398.0 m/e; $^1$H NMR (400 MHz, CDCl$_3$) ☐ 0.82 (t, 3H, J=7.5); 1.17 (s, 3H); 1.27 (s, 3H); 1.72 (m, 2H); 1.88 (s, 3H); 1.94 (s, 3H); 3.20 (m, 3H); 3.29 (dd, 1H, J=5.9, 12.2); 4.39 (m, 2H); 4.97 (dd, 1H, J=1.2, 5.9); 6.86 (d, 1H, J=3.3); 6.94 (dd, 1H, J=3.4, 5.1); 7.17 (dd, 1H, J=1.1, 5.1).

Example 15

Synthesis of 3-(3-pyridyl)-1-propyl (2S)-5,5-dimethyl-1-(3,3-dimethyl-1,2-dioxobutyl)-2-(4-thiazolidine)carboxylate The title compound was prepared in the same manner as described in example 1 wherein $R_3MgY$ used is t-butyl magnesium chloride solution in ethyl ether (2.0M), and $R_4OH$ used is 3-(3-pyridyl)-1-propanol. MS [M+H]$^+$=393.4 m/e; $^1$H NMR (400 MHz, CDCl$_3$) ☐ 1.29 (s, 9H); 1.91 (s, 3H); 1.98 (s, 3H); 2.01 (m, 2H); 2.72 (t, 2H, J=7.5); 3.26 (dd, 1H, J=1.5, 12.2); 3.33 (dd, 1H, J=5.8, 12.2); 4.21 (m, 2H); 5.00 (dd, 1H, J=1.5, 5.8); 7.25 (m, 1H); 7.54 (m, 1H); 8.47 (m, 2H).

Example 16

Synthesis of 3-(6-methyl-2-pyridyl)-1-propyl (2S)-5,5-dimethyl-1-(3,3-dimethyl-1,2-dioxobutyl)-2-(4-thiazolidine)carboxylate The title compound was prepared in the same manner as described in example 1 wherein $R_3MgY$ used is the same as that used in example 15, and $R_4OH$ used is 3-(6-methyl-2-pyridyl)-1-propanol. MS [M+H]$^+$=407.2 m/e; $^1$H NMR (400 MHz, CDCl$_3$) ☐ 1.28 (s, 9H); 1.89 (s, 3H); 1.97 (s, 3H); 2.11 (m, 2H); 2.53 (s, 3H); 2.83 (t, 2H, J=7.9); 3.27 (dd, 1H, J=1.9, 12.3); 3.32 (dd, 1H, J=5.5, 12.3); 4.21 (m, 2H); 5.03 (dd, 1H, J=1.9, 5.5); 6.98 (m, 2H); 7.50 (t, 1H, J=7.7).

Example 17

Synthesis of 3-phenyl-1-propyl (2S)-5,5-dimethyl-1-(3,3-dimethyl-1,2-dioxobutyl)-2-(4-thiazolidine)carboxylate The title compound was prepared in the same manner as described in example 1 wherein $R_3MgY$ used is the same as that used in example 15, and $R_4OH$ used is 3-phenyl-1-propanol. MS [M+H]$^+$=392.4 m/e; $^1$H NMR (400 MHz, CDCl$_3$) ☐ 1.28 (s, 9H); 1.90 (s, 3H); 1.97 (s, 3H); 2.00 (m, 2H); 2.69 (t, 2H, J=7.4); 3.24 (dd, 1H, J=1.4, 12.3); 3.31 (dd, 1H, J=5.8, 12.3); 4.19 (m, 2H); 5.02 (dd, 1H, J=1.4, 5.8); 7.19 (m, 3H); 7.29 (m, 2H).

Example 18

Synthesis of (E)-3-phenyl-prop-2-en-1-yl (2S)-5,5-dimethyl-1-(3,3-dimethyl-1,2-dioxobutyl)-2-(4-thiazolidine)carboxylate The title compound was prepared in the same manner as described in example 1 wherein $R_3MgY$ used is the same as that used in example 15, and $R_4OH$ used is (E)-3-phenyl-prop-2-en-1-ol. MS [M+H]$^+$=390.2 m/e; $^1$H NMR (400 MHz, CDCl$_3$) ☐ 1.28 (s, 9H); 1.90 (s, 3H); 1.97 (s, 3H); 3.34 (d, 2H, J=3.7); 4.78 (ddd, 1H, J=1.2, 6.5, 12.7); 4.85 (ddd, J=1.2, 6.5, 12.7); 5.13 (t, 1H, J=3.7); 6.25 (dt, 1H, J=6.5, 15.9); 6.67 (d, 1H, J=15.9); 7.26-7.40 (m, 5H).

Example 19

Synthesis of 1-phenoxy-2-propyl (2S)-5,5-dimethyl-1-(3,3-dimethyl-1,2-dioxobutyl)-2-(4-thiazolidine)carboxylate The title compound was prepared in the same manner as described in example 1 wherein $R_3MgY$ used is the same as that used in example 15, and $R_4OH$ used is 1-phenoxy-2-propanol. MS [M+H]$^+$=408.3 m/e; $^1$H NMR (400 MHz, CDCl$_3$) ☐ 1.27 (d, 3H, J=2.3); 1.28 (s, 9H); 1.88 (s, 3H); 1.94 (s, 3H); 3.29 (m, 2H); 4.30 (m, 2H); 5.01 (m, 1H); 5.31 (m, 1H); 6.93 (m, 3H); 7.28 (m, 2H).

Example 20

Synthesis of 3-cyclohexyl-1-propyl (2S)-5,5-dimethyl-1-(3,3-dimethyl-1,2-dioxobutyl)-2-(4-thiazolidine)carboxylate The title compound was prepared in the same manner as described in example 1 wherein $R_3MgY$ used is the same as that used in example 15, and R$_4$OH used is 3-cyclohexyl-1-propanol. MS [M+H]$^+$=398.3 m/e; $^1$H NMR (400 MHz, CDCl$_3$) ☐ 0.87 (m, 2H); 1.11-1.26 (m, 6H); 1.28 (s, 9H); 1.62-1.70 (m, 7H); 1.89 (s, 3H); 1.95 (s, 3H); 3.28 (dd, 1H, J=2.1, 12.2); 3.32 (dd, 1H, J=5.4, 12.2); 4.14 (m, 2H); 5.04 (dd, 1, J=2.1, 5.4).

Example 21

Synthesis of (1R)-1-(4-methoxyphenyl)-3-phenyl-1-propyl (2S)-5,5-dimethyl-1-(3,3-dimethyl-1,2-dioxobutyl)-2-(4-thiazolidine)carboxylate The title compound was prepared in the same manner as described in example 1 wherein R$_3$MgY used is the same as that used in example 15, and R$_4$OH used is (1R)-1-(4-methoxyphenyl)-3-phenyl-1-propanol. MS [M+H]$^+$=498.1 m/e; $^1$H NMR (400 MHz, CDCl$_3$) ☐ 1.01 (s, 9H); 1.88 (s, 3H); 1.95 (s, 3H); 2.11 (m, 1H); 2.31 (m, 1H); 2.61 (m, 2H); 3.26 (dd, 1H, J=1.4, 12.3); 3.33 (dd, 1H, J=5.8, 12.3); 3.80 (s, 3H); 5.02 (dd, 1H, J=1.4, 5.8); 5.69 (dd, 1H, J=6.0, 8.0); 6.85 (m, 2H); 7.14-7.29 (m, 7H).

Example 22

Synthesis of 3-(N,N-dibenzylamino)-1-propyl (2S)-5,5-dimethyl-1-(3,3-dimethyl-1,2-dioxobutyl)-2-(4-thiazolidine)carboxylate The title compound was prepared in the same manner as described in example 1 wherein R$_3$MgY used is the same as that used in example 15, and R$_4$OH used is 3-(N,N-dibenzylamino)-1-propanol. MS [M+H]$^+$=511.3 m/e; $^1$H NMR (400 MHz, CDCl$_3$) ☐ 1.27 (s, 9H); 1.82 (m, 2H); 1.86 (s, 3H); 1.90 (s, 3H); 2.49 (t, 2H, J=6.7); 2.93 (d, 1H, J=12.3); 3.14 (dd, 1H, J=6.0, 12.3); 3.54 (s, 4H); 4.19 (m, 2H); 4.92 (d, 1H, J=6.0); 7.22-7.35 (m, 10H).

Example 23

Synthesis of dec-9-en-1-yl (2S)-5,5-dimethyl-1-(3,3-dimethyl-1,2-dioxobuiyl)-2-(4-thiazolidine)carboxylate The title compound was prepared in the same manner as described in example 1 wherein R$_3$MgY used is the same as that used in example 15, and R$_4$OH used is dec-9-en-1-ol. MS [M+H]$^+$=412.4 m/e; $^1$H NMR (400 MHz, CDCl$_3$) ☐ 1.28 (s, 9H); 1.28-1.37 (m, 10H); 1.64 (m, 2H); 1.89 (s, 3H); 1.96 (s, 3H); 2.04 (m, 2H); 3.28 (dd, 1H, J=2.1, 12.2); 3.32 (dd, 1H, J=5.4, 12.2); 4.15 (m, 2H); 4.93 (dd, 1H, J=2.0, 12.2); 4.99 (dd, 1H, J=2.0, 15.5); 5.04 (dd, 1H, J=2.1, 5.4); 5.79 (ddt, 1H, J=6.7, 12.2, 15.5).

Example 24

Synthesis of (2R)-1-methoxy-2-propyl (2S)-5,5-dimethyl-1-(3,3-dimethyl-1,2-dioxobutyl)-2-(4-thiazolidine)carboxylate The title compound was prepared in the same manner as described in example 1 wherein R$_3$MgY used is the same as that used in example 15, and R$_4$OH used is (2R)-1-methoxy-2-propanol. MS [M+H]$^+$=346.1 m/e; $^1$H NMR (400 MHz, CDCl$_3$) ☐ 1.27 (m, 12H); 1.89 (s, 3H); 1.96 (s, 3H); 3.30 (m, 2H); 3.34 (s, 3H); 3.43 (m, 2H); 5.02 (dd, 1, J=2.5, 4.9); 5.13 (m, 1H).

Example 25

Synthesis of 3-(3-pyridyl)-1-propyl (2S)-5,5-dimethyl-1-(1,2-dioxooctyl)-2-(4-thiazolidine)carboxylate The title compound was prepared in the same manner as described in example 1 wherein R$_3$MgY used is n-hexyl magnesium bromide solution in ethyl ether (2.0M), and R$_4$OH used is 3-(3-pyridyl)-1-propanol. MS [M+H]$^+$=421.3 m/e; $^1$H NMR (400 MHz, CDCl$_3$) ☐ 0.87 (m, 3H); 1.28 (m, 6H); 1.54 (m, 2H); 1.87 (s, 3H); 1.97 (s, 3H); 2.00 (m, 2H); 2.71 (t, 2H, J=7.1); 2.73 (m, 1H); 2.99 (m, 1H); 3.31 (m, 2H); 4.19 (m, 2H); 5.42 (dd, 1H, J=2.8, 5.2); 7.26 (m, 1H); 7.54 (m, 1H); 8.48 (m, 2H).

Example 26

Synthesis 3-(6-methyl-2-pyridyl)-1-propyl (2S)-5,5-dimethyl-1-(1,2-dioxooctyl)-2-(4-thiazolidine)carboxylate The title compound was prepared in the same manner as described in example 1 wherein R$_3$MgY used is the same as that used in example 25, and R$_4$OH used is 3-(6-methyl-2-pyridyl)-1-propanol. MS [M+H]$^+$=435.0 m/e; $^1$H NMR (400 MHz, CDCl$_3$) ☐ 0.87 (m, 3H); 1.27 (m, 6H); 1.54 (m, 2H); 1.86 (s, 3H); 1.93 (s, 3H); 2.10 (m, 2H); 2.55 (s, 3H); 2.72 (m, 1H); 2.84 (m, 2H); 3.01 (m, 1H); 3.32 (m, 2H); 4.20 (m, 2H); 5.42 (dd, 1H, J=3.2, 4.8); 6.99 (m, 2H); 7.52 (m, 1H).

Example 27

Synthesis of 3-phenyl-1-propyl (2S)-5,5-dimethyl-1-(1,2-dioxooctyl)-2-(4-thiazolidine)carboxylate The title compound was prepared in the same manner as described in example 1 wherein R$_3$MgY used is the same as that used in example 25, and R$_4$OH used is 3-phenyl-1-propanol. MS [M+H]$^+$=420.1 m/e; $^1$H NMR (400 MHz, CDCl$_3$) ☐ 0.87 (m, 3H); 1.27 (m, 6H); 1.54 (m, 2H); 1.86 (s, 3H); 1.93 (s, 3H); 1.98 (m, 2H); 2.69 (t, 2H, J=7.4); 2.70 (m, 1H); 2.99 (m, 1H); 3.30 (m, 2H); 4.17 (m, 2H); 5.43 (dd, 1H, J=3.3, 4.5); 7.19 (m, 3H); 7.29 (m, 2H).

Example 28

Synthesis of (E)-3-phenyl-prop-2-en-1-yl (2S)-5,5-dimethyl-1-(1,2-dioxooctyl)-2-(4-thiazolidine)carboxylate The title compound was prepared in the same manner as described in example 1 wherein R$_3$MgY used is the same as that used in example 25, and R$_4$OH used is (E)-3-phenyl-prop-2-en-1-ol. MS [M+H]$^+$=418.1 m/e; $^1$H NMR (400 MHz, CDCl$_3$) ☐ 0.87 (m, 3H); 1.27 (m, 6H); 1.53 (m, 2H); 1.86 (s, 3H); 1.93 (s, 3H); 2.72 (m, 1H); 3.02 (m, 1H); 3.33 (dd, 1H, J=5.8, 12.2); 3.38 (dd, 1H, J=2.2, 12.2); 4.80 (m, 2H); 5.50 (dd, 1H, J=2.2, 5.8); 6.23 (dt, 1H, J=6.4, 15.9); 6.66 (d, 1H, J=15.9); 7.33 (m, 5H).

Example 29

Synthesis of 2-(2-chlorophenyl)-1-ethyl (2S)-5,5-dimethyl-1-(1,2-dioxooctyl)-2-(4-thiazolidine)carboxylate The title compound was prepared in the same manner as described in example 1 wherein R$_3$MgY used is the same as that used in example 25, and R$_4$OH used is 2-(2-chlorophenyl)-1-ethanol. MS [M+H]$^+$=440.0 m/e; $^1$H NMR (400 MHz, CDCl$_3$) □ 0.87 (m, 3H); 1.29 (m, 6H); 1.53 (m, 2H); 1.84 (s, 3H); 1.89 (s, 3H); 2.66 (m, 1H); 2.98 (m, 1H); 3.09 (t, 2H, J=6.8); 3.26 (m, 2H); 4.40 (t, 2H, J=6.8); 5.40 (dd, 1H), J=3.2, 4.9); 7.21 (m, 3H); 7.37 (m, 1H).

Example 30

Synthesis of 3-(3-pyridyl)-1-propyl (2S)-5,5-dimethyl-1-(1,2-dioxodecyl)-2-(4-thiazolidine)carboxylate The title compound was prepared in the same manner as described in example 1 wherein R$_3$MgY used is n-octyl magnesium bromide solution in THF (2.0M), and R$_4$OH used is 3-(3-pyridyl)-1-propanol. MS [M+H]$^+$=449.2 m/e; $^1$H NMR (600 MHz, CDCl$_3$) □ 0.87 (t, 3H, J=7.2); 1.29 (m, 10H); 1.55 (m, 2H); 1.87 (s, 3H); 1.94 (s, 3H); 2.01 (m, 2H); 2.70 (t, 2H, J=7.8); 2.74 (m, 1H); 3.01 (m, 1H); 3.32 (m, 2H); 4.20 (m, 2H); 5.43 (dd, 1H, J=2.4, 5.4); 7.25 (m, 1H); 7.53 (d, 1H, J=7.8); 8.48 (s, 2H).

Example 31

Synthesis of 3-(6-methyl-2-pyridyl)-1-propyl (2S)-5,5-dimethyl-1-(1,2-dioxodecyl)-2-(4-thiazolidine)carboxylate The title compound was prepared in the same manner as described in example 1 wherein R$_3$MgY used is the same as that used in example 30, and R$_4$OH used is 3-(6-methyl-2-pyridyl)-1-propanol. MS [M+H]$^+$=463.2 m/e; $^1$H NMR (600 MHz, CDCl$_3$) □ 0.87 (t, 3H, J=7.2); 1.28 (m, 10H); 1.54 (m, 2H); 1.86 (s, 3H); 1.93 (s, 3H); 2.10 (m, 2H); 2.53 (m, 2H); 2.70 (m, 1H); 2.82 (t, 2H, J=7.8); 3.00 (m, 1H); 3.31 (m, 2H); 4.21 (m, 2H); 5.42 (dd, 1H, J=3.0, 4.8); 6.96 (dd, 2H, J=7.8, 24.0); 7.50 (t, 1H, J=7.8).

Example 32

Synthesis of 2-(2-chlorophenyl)-1-ethyl (2S)-5,5-dimethyl-1-(1,2-dioxodecyl)-2-(4-thiazolidine)carboxylate The title compound was prepared in the same manner as described in example 1 wherein R$_3$MgY used is the same as that used in example 30, and R$_4$OH used is 2-(2-chlorophenyl)-1-ethanol. MS [M+H]$^+$=468.3 m/e; $^1$H NMR (600 MHz, CDCl$_3$) □ 0.87 (t, 3H, J=7.2); 1.27 (m, 10H); 1.53 (m, 2H); 1.84 (s, 3H); 1.89 (s, 3H); 2.67 (m, 1H); 2.98 (m, 1H); 3.09 (t, 2H, J=6.6); 3.28 (m, 2H); 4.39 (t, 2H, J=6.6); 5.40 (dd, 1H, J=3.6, 6.0); 7.20 (m, 3H); 7.36 (m, 1H).

Example 33

Synthesis of (2R)-1-methoxy-2-propyl (2S)-5,5-dimethyl-1-(1,2-dioxodecyl)-2-(4-thiazolidine)carboxylate The title compound was prepared in the same manner as described in example 1 wherein R$_3$MgY used is the same as that used in example 30, and R$_4$OH used is (2R)-1-methoxy-2-propanol. MS [M+H]$^+$=402.1 m/e; $^1$H NMR (600 MHz, CDCl$_3$) □ 0.87 (t, 3H, J=7.2); 1.23 (m, 13H); 1.55 (m, 2H); 1.86 (s, 3H); 1.92 (s, 3H); 2.70 (m, 1H); 3.03 (m, 1H); 3.29 (m, 2H); 3.35 (s, 3H); 3.41 (m, 2H); 5.10 (m, 1H); 5.43 (m, 1H).

Example 34

Synthesis of 2-pentyl (2S)-5,5-dimethyl-1-(1,2-dioxodecyl)-2-(4-thiazolidine)carboxylate The title compound was prepared in the same manner as described in example 1 wherein R$_3$MgY used is the same as that used in example 30, and R$_4$OH used is 2-pentanol. MS [M+H]$^+$=400.1 m/e; $^1$H NMR (600 MHz, CDCl$_3$) □ 0.87 (t, 3H, J=7.2); 0.91 (m, 3H); 1.21 (t, 3H, J=7.8); 1.26-1.38 (m, 12H); 1.44-1.61 (m, 4H); 1.86 (s, 3H); 1.92 (s, 3H); 2.71 (m, 1H); 3.03 (m, 1H); 3.31 (m, 2H); 4.95 (m, 1H); 5.41 (m, 1).

Example 35

Synthesis of 3-(3-pyridyl)-1-propyl (2S)-5,5-dimethyl-1-(1,2-dioxo-2-phenyl)ethyl-2-(4-thiazolidine)carboxylate The title compound was prepared in the same manner as described in example 1 wherein R$_3$MgY used is phenyl magnesium bromide solution in THF (1.0M), and R$_4$OH used is 3-(3-pyridyl)-1-propanol. MS [M+H]$^+$=413.3 m/e; $^1$H NMR (400 MHz, CDCl$_3$) □ 1.80 (m, 2H); 1.99 (s, 3H); 2.09 (s, 3H); 2.57 (m, 2H); 3.31 (dd, 1H, J=1.5, 12.2); 3.39 (dd, 1H, J=5.8, 12.2); 3.98 (dt, 1H, J=6.4, 10.9); 4.07 (dt, 1H, J=6.4, 10.9); 5.20 (dd, 1H, J=1.5, 5.8); 7.22 (m, 1H); 7.42-7.60 (m, 5H); 8.01 (m, 1H); 8.45 (m, 2H).

Example 36

Synthesis of 3-phenyl-1-propyl (2S)-5,5-dimethyl-1-(1,2-dioxo-2-phenyl)ethyl-2-(4-thiazolidine)carboxylate The title compound was prepared in the same manner as described in example 1 wherein R$_3$MgY used is the same as that used in example 35, and R$_4$OH used is 3-phenyl-1-propanol. MS [M+H]$^+$=412.4 m/e; $^1$H NMR (400 MHz, CDCl$_3$) □ 1.80 (m, 2H); 1.99 (s, 3H); 2.09 (s, 3H); 2.56 (m, 2H); 3.30 (dd, 1H, J=1.4, 12.1); 3.38 (dd, 1H, J=5.8, 12.1); 3.93 (dt, 1H, J=6.5, 10.9); 4.05 (dt, 1H, J=6.5, 10.9); 5.20 (dd, 1H, J=1.4, 5.8); 7.09-8.03 (m, 10H).

Example 37

Synthesis of (E)-3-phenyl-prop-2-en-1-yl (2S)-5,5-dimethyl-1-(1,2-dioxo-2-phenyl)ethyl-2-(4-thiazolidine)carboxylate The title compound was prepared in the same manner as described in example 1 wherein R$_3$MgY used is the same as that used in example 35, and R$_4$OH used is (E)-3-phenyl-prop-2-en-1-ol. MS [M+H]$^+$=410.4 m/e; $^1$H NMR (400 MHz, CDCl$_3$) □ 1.98 (s, 3H); 2.09 (s, 3H); 3.39 (d, 2H, J=3.9); 4.54 (ddd, 1H, J=1.2, 6.6, 12.7); 4.64 (m, 1H); 5.28 (t, 1H, J=3.9); 5.99 (dt, 1, J=6.6, 15.9); 6.49 (d, 1H, J=15.9); 7.26-8.03 (m, 10H).

Example 38

Synthesis of 3-cyclohexyl-1-propyl (2S)-5,5-dimethyl-1-(1,2-dioxo-2-phenyl)ethyl-2-(4-thiazolidine)carboxylate The title compound was prepared in the same manner as described in example 1 wherein R$_3$MgY used is the same as that used in example 35, and R₄OH used is 3-cyclohexyl-1-propanol. MS [M+H]⁺=418.4 m/e; ¹H NMR (400 MHz, CDCl₃) ☐ 0.79-1.82 (m, 15H); 1.98 (s, 3H); 2.08 (s, 3H); 3.34 (dd, 1H, J=1.9, 12.2); 3.38 (dd, 1H, J=5.4, 12.2); 3.85 (dt, 1H, J=6.9, 10.6); 3.98 (dt, 1H, J=6.9, 10.6); 5.22 (dd, 1H, J=1.9, 5.4); 7.42-8.08 (m, 5H).

Example 39

Synthesis of dec-9-en-1-yl (2S)-5,5-dimethyl-1-(1, 2-dioxo-2-phenyl)ethyl-2-(4-thiazolidine)carboxylate The title compound was prepared in the same manner as described in example 1 wherein R₃MgY used is the same as that used in example 35, and R₄OH used is dec-9-en-1-ol. MS [M+H]⁺=432.4 m/e; ¹H NMR (400 MHz, CDCl₃) ☐ 1.20-1.44 (m, 12H); 1.98 (s, 3H); 2.03 (m, 2H); 2.07 (s, 3H); 3.33 (dd, 1H, J=1.9, 12.1); 3.38 (dd, 1H, J=5.4, 12.1); 3.87 (dt, 1H, J=6.8, 10.7); 3.99 (dt, 1H, J=6.8, 10.7); 4.97 (m, 2H); 5.22 (dd, 1H, J=1.9, 5.4); 5.79 (m, 1H); 7.47 (m, 2H); 7.61 (m, 1H); 8.02 (m, 2H).

Example 40

Synthesis of 3-(3-pyridyl)-1-propyl (2S)-5,5-dimethyl-1-[2-(4-chlorophenyl)-1,2-dioxoethyl]-2-(4-thiazolidine)carboxylate The title compound was prepared in the same manner as described in example 1 wherein R₃MgY used is 4-chlorophenyl magnesium bromide solution in ethyl ether (1.0M), and R₄OH used is 3-(3-pyridyl)-1-propanol. MS [M+H]⁺=447.2 m/e; ¹H NMR (600 MHz, CDCl₃) ☐ 1.83 (m, 2H); 1.97 (s, 3H); 2.07 (s, 3H); 2.58 (m, 2H); 3.36 (m, 2H); 4.07 (m, 2H); 5.26 (m, 1); 7.23 (m, 1); 7.49 (m, 3H); 7.99 (m, 2H,); 8.45 (m, 2H).

Example 41

Synthesis of 3-(3-pyridyl)-1-propyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R₃MgY used is 2,4,6-trimethylphenyl magnesium bromide solution in THF (1.0M), and R₄OH used is 3-(3-pyridyl)-1-propanol. MS [M+H]⁺=455.1 m/e; ¹H NMR (400 MHz, CDCl₃) ☐ 1.92 (s, 3H); 2.03 (s, 3H); 2.04 (m, 2H); 2.25 (s, 6H); 2.28 (s, 3H); 2.75 (t, 2H, J=7.7); 3.31 (dd, 1H, J=1.2, 12.3); 3.39 (dd, 1H, J=6.0, 12.3); 4.28 (m, 2H); 5.36 (dd, 1H, J=1.2, 6.0); 6.85 (s, 2H); 7.22 (m, 1H); 7.55 (m, 1H); 8.48 (m, 2H).

Example 42

Synthesis of 3-phenyl-1-propyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R₃MgY used is the same as that used in example 41, and R₄OH used is and 3-phenyl-1-propanol. MS [M+H]⁺=454.2 m/e; ¹H NMR (400 MHz, CDCl₃) ☐ 1.92 (s, 3H); 2.02 (m, 2H); 2.03 (s, 3H); 2.25 (s, 6H); 2.28 (s, 3H); 2.73 (t, 2H, J=7.5); 3.30 (dd, 1H, J=1.2, 12.2); 3.37 (dd, 1H, J=6.1, 12.2); 4.25 (m, 2H); 5.37 (dd, 1H, J=1.2, 6.1); 6.85 (s, 2H); 7.20 (m, 3H); 7.28 (m, 2H).

Example 43

Synthesis of (E)-3-phenyl-prop-2-en-1-yl (2S)-5,5-dimethyl-1-[1,2-dioxo-2-(2,4,6-trimethylphenyl)] ethyl-2-(thiazolidine)carboxylate The title compound was prepared in the same manner as described in example 1 wherein R₃MgY used is the same as that used in example 41, and R₄OH used is (E)-3-phenyl-prop-2-en-1-ol. MS [M+H]⁺=452.1 m/e; ¹H NMR (400 MHz, CDCl₃) ☐ 1.91 (s, 3H); 2.02 (s, 3H); 2.24 (s, 6H); 2.27 (s, 3H); 3.38 (m, 2H); 4.88 (m, 2H); 5.45 (dd, 1H, J=2.6, 5.0); 6.30 (dt, 1H, J=6.4, 15.9); 6.70 (d, 1H, J=15.9); 6.86 (m, 3H); 7.30 (m, 4H).

Example 44

Synthesis of 3-cyclohexyl-1-propyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R₃MgY used is the same as that used in example 41, and R₄OH used is 3-cyclohexyl-1-propanol. MS [M+H]⁺=460.2 m/e; ¹H NMR (400 MHz, CDCl₃) ☐ 0.87 (m, 2H); 1.11-1.28 (m, 6H); 1.60-1.70 (m, 7H); 1.91 (s, 3H); 2.01 (s, 3H); 2.25 (s, 6H); 2.28 (s, 3H); 3.32 (dd, 1H, J=1.7, 12.2); 3.37 (dd, 1H, J=5.6, 12.2); 4.20 (m, 2H); 5.38 (dd, 1H, J=1.7, 5.6); 6.85 (s, 2H).

Example 45

Synthesis of 3-phenoxy-1-propyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R₃MgY used is the same as that used in example 41, and R₄OH used is 3-phenoxy-1-propanol. MS [M+H]⁺=470.1 m/e; ¹H NMR (400 MHz, CDCl₃) ☐ 1.90 (s, 3H); 1.99 (s, 3H); 2.19 (m, 2H); 2.23 (s, 6H); 2.28 (s, 3H); 3.30 (dd, 1H, J=1.3, 12.3); 3.36 (dd, 1H, J=5.8, 12.3); 4.08 (m, 2H); 4.45 (m, 2H); 5.35 (dd, 1H, J=1.3, 5.8); 6.84 (s, 2H); 6.94 (m 3H); 7.26 (m, 2H).

Example 46

Synthesis of 2-(2-thienyl)-1-ethyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R₃MgY used is the same as that used in example 41, and R₄OH used is 2-(2-thienyl)-1-ethanol. MS [M+H]⁺=446.1 m/e; ¹H NMR (400 MHz, CDCl₃) ☐ 1.90 (s, 3H); 1.98 (s, 3H); 2.25 (s, 6H); 2.28 (s, 3H); 3.23 (t, 2H, J=6.8); 3.26 (dd, 1H, J=1.3, 12.3); 3.35 (dd, 1H, J=6.1, 12.3); 4.46 (m, 2H); 5.38 (dd, 1H, J=1.3, 6.1); 6.85 (s, 2H); 6.84-6.94 (m, 4H); 7.15 (m, 1H).

Example 47

Synthesis of 2-aminobenzyl (2S)-5,5-dimethyl-1-[1, 2-dioxo-2-(2,4,6-trimethylphenyl)]ethyl-2-(4-thiazolidine)carboxylate The title compound was prepared in the same manner as described in example 1 wherein R₃MgY used is the same as that used in example 41, and R₄OH used is 2-aminobenzyl alcohol. MS [M+H]$^+$=441.1 m/e; $^1$H NMR (400 MHz, CDCl$_3$) ☐ 1.89 (s, 3H); 1.96 (s, 3H); 2.22 (s, 6H); 2.28 (s, 3H); 3.31 (dd, 1H, J=1.5, 12.4); 3.36 (dd, 1H, J=5.8, 12.4); 3.48-5.05 (br, 2H); 5.23 (m, 2H); 5.29 (dd, 1H, J=1.5, 5.8); 6.74 (m, 2H); 6.84 (s, 2H); 7.17 (m, 2H).

Example 48

Synthesis of 2-(N-benzyl-N-methyl)amino-1-ethyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R$_3$MgY used is the same as that used in example 41, and R$_4$OH used is 2-(N-benzyl-N-methyl)amino-1-ethanol. MS [M+H]$^+$=483.2 m/e; $^1$H NMR (400 MHz, CDCl$_3$) ☐ 1.91 (s, 3H); 2.01 (s, 3H); 2.24 (s, 6H); 2.28 (s, 6H); 2.77 (m, 2H); 3.30 (dd, 1H, J=1.5, 12.3); 3.36 (dd, 1H, J=5.8, 12.3); 3.58 (m, 2H); 4.37 (m, 2H); 5.38 (dd, 1H, J=1.5, 5.8); 6.84 (s, 2H); 7.25 (m, 1H); 7.30 (m, 4H).

Example 49

Synthesis of 1-phenoxy-2-propyl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R$_3$MgY used is the same as that used in example 41, and R$_4$OH used is 1-phenoxy-2-propanol. MS [M+H]$^+$=470.1 m/e; $^1$H NMR (400 MHz, CDCl$_3$) ☐ 1.32 (m, 3H); 1.90 (s, 3H); 2.04 (s, 3H); 2.25 (s, 6H); 2.28 (s, 3H); 3.28 (dd, 1H, J=3.5, 12.7); 3.42 (dd, 1H, J=6.8, 12.7); 3.67 (m, 2H); 4.16 (m, 1H); 5.45 (dd, 1H, J=3.5, 6.8); 6.89 (m, 5H); 7.26 (m, 2H).

Example 50

Synthesis of dec-9-en-1-yl (2S)-5,5-dimethyl-1-[1,2-dioxo-2-(2,4,6-trimethylphenyl)]ethyl-2-(4-thiazolidine)carboxylate The title compound was prepared in the same manner as described in example 1 wherein R$_3$MgY used is the same as that used in example 41, and R$_4$OH used is dec-9-en-1-ol. MS [M+H]$^+$=474.2 m/e; $^1$H NMR (400 MHz, CDCl$_3$) ☐ 1.28-1.38 (m, 10H); 1.67 (m, 2H); 1.91 (s, 3H); 2.01 (s, 3H); 2.02 (m, 2H); 2.25 (s, 6H); 2.28 (s, 3H); 3.32 (dd, 1H, J=1.6, 12.3); 3.37 (dd, 1H, J=5.7, 12.3); 4.22 (m, 2H); 4.93 (dd, 1H, J=1.8, 10.2); 4.99 (dd, 1H, J=1.8, 17.1); 5.38 (dd, 1H, J=1.6, 5.7); 5.80 (ddt, 1H, J=6.7, 10.2, 17.1); 6.85 (s, 2H).

Example 51

Synthesis of 3-(3-pyridyl)-1-propyl (2S)-5,5-dimethyl-1-(1,2-dioxo-4-methyl-4-phenyl)pentyl-2-(4-thiazolidine)carboxylate The title compound was prepared in the same manner as described in example 1 wherein R$_3$MgY used is 2-methyl-2-phenylpropyl magnesium chloride solution in ethyl ether (0.5M), and R$_4$OH used is 3-(3-pyridyl)-1-propanol. MS [M+H]$^+$=469.1 m/e; $^1$H NMR (600 MHz, CDCl$_3$) ☐ 1.41 (s, 3H); 1.44 (s, 3H); 1.71 (s, 3H); 1.88 (s, 3H); 1.96 (m, 2H); 2.67 (t, 2H, J=7.8); 2.74 (d, 1H, J=16.2); 2.97 (dd, 1H, J=6.0, 12.0); 3.07 (d, 1H, J=12.0); 3.82 (d, 1H, J=16.2); 4.15 (m, 2H); 4.59 (d, 1H, J=6.0); 7.18-7.36 (m, 7H); 8.47 (m, 2H)).

Example 52

Synthesis of 2-phenylbenzyl (2S)-5,5-dimethyl-1-(1,2-dioxo-4-methyl-4-phenyl)pentyl-2-(4-thiazolidine)carboxylate The title compound was prepared in the same manner as described in example 1 wherein R$_3$MgY used is the same as that used in example 51, and R$_4$OH used is 2-phenylbenzyl alcohol. MS [M+H]$^+$=516.3 m/e; $^1$H NMR (600 MHz, CDCl$_3$) ☐1.37 (s, 3H); 1.39 (s, 3H); 1.71 (s, 3H); 1.82 (s, 3H); 2.73 (d, 1H, J=16.2); 2.96-2.97 (dd, 1H, J=6.0, 12.0); 3.02 (d, 1H, J=12.0); 3.75 (d, 1H, J=16.2); 4.77 (d, 1H, J=6.0); 5.04 (d, 1H, J=12.0); 5.11 (d, 1H, J=12.0); 7.16-7.44 (m, 14H).

Example 53

Synthesis of 3-(3-pyridyl)-1-propyl (2S)-5,5-dimethyl-1-(3,3-dimethyl-1,2-dioxopentyl)-2-(4-oxazolidine)carboxylate The starting material is L-cysteine methyl ester hydrochloride. The title compound was prepared in the same manner as described in example 1 wherein R$_3$MgY used is 1,1-dimethylpropyl magnesium chloride solution in ethyl ether (1.0M), and R$_4$OH used is 3-(3-pyridyl)-1-propanol. MS [M+H]$^+$=391.3 m/e; $^1$H NMR (600 MHz, CDCl$_3$) ☐ 0.82 (t, 3H, J=7.2); 1.18 (s, 3H); 1.29 (s, 3H); 1.62 (s, 3H); 1.74 (s, 3H); 1.76 (m, 2H); 2.02 (m, 2H); 2.71 (t, 2H, J=7.8); 4.15-4.26 (m, 4H); 4.69 (dd, 1H, J=3.0, 4.8); 7.24 (m, 1H); 7.53 (d, 1H, J=7.8); 8.47 (s, 2H).

Example 54

Synthesis of 3-phenyl-1-propyl (2S)-5,5-dimethyl-1-(3,3-dimethyl-1,2-dioxopentyl)-2-(4-oxazolidine)carboxylate The starting material is L-cysteine methyl ester hydrochloride. The title compound was prepared in the same manner as described in example 1 wherein R$_3$MgY used is 1,1-dimethylpropyl magnesium chloride solution in ethyl ether (1.0M), and R$_4$OH used is 3-phenyl-1-propanol. MS [M+Na]$^+$=412.3 m/e; $^1$H NMR (600 MHz, CDCl$_3$) ☐ 0.82 (t, 3H, J=7.8); 1.18 (s, 3H); 1.30 (s, 3H); 1.62 (s, 3H); 1.71 (m, 1H); 1.75 (s, 3H); 1.82 (m, 1H); 1.99 (m, 2H); 2.69 (t, 2H, J=7.8); 4.16-4.19 (m, 4H); 4.72 (dd, 1H, J=3.0, 5.4); 7.17-7.30 (m, 5H).

Example 55

The neurotrophic activity of compounds of the present invention can be determined through several biological models in vitro, e.g. the model of chick embryos dorsal root ganglion cultures free of serum in vitro.

In a sterile environment, dorsal root ganglia were dissected from chick embryos of 8 days gestation and inoculated in rat rail collagen coated culture bottles (5 to 6 dorsal root ganglia per bottle, and two bottles per dosage). After 1 hour of attachment in a 37° C., 5% CO$_2$ incubator, NGF (0.15 ng/ml) containing culture medium free of serum (DMEM) and the compound of the present invention were added. The control groups were treated only with the same amount of NGF and culture medium. After further incubated in a incubator as described above for 48 h, the ganglia were observed for growth of the processes around dorsal root ganglia under phase contrast with an inverted microscope, and were scored based on the neurite processes (ganglion with free processes: 0; ganglion with rare processes: 1; ganglion with long or dense processes: 2; ganglion with very long or dense processes: 3). Five to six DRGs were cultured per bottle, and each treatment was performed in duplicate. The results of illustrative compound of example 15 promoting the growth of chick embryos dorsal root ganglia processes were outlined in table 1, wherein the scoring is the average scoring of 10 ganglia.

TABLE 1

| Groups | Average scoring |
|---|---|
| culture medium + NGF (0.15 ng/mL) (control groups) | 0.33 |
| DMEM + compound of example 15 (1 pM) + NGF (0.15 ng/mL) | 1.00 |
| DMEM + compound of example 15 (10 pM) + NGF (0.15 ng/mL) | 1.31 |
| DMEM + compound of example 15 (100 pM) + NGF (0.15 ng/mL) | 1.57 |

FIG. 1 indicates the growth of neurites of chick dorsal root ganglia under various dosages of the compound of example 15. A represents that chick embryos dorsal root ganglia with rare processes is caused by the treatment of sole NGF (0.15 ng/mL). B represents that the compound of example 15 (1 pM) enhances the improving effect of sole NGF (0.15 ng/mL) on the growth of neurites. C represents that the compound of example 15 having a concentration of 10 pM exhibits a stronger effect on the growth of neurites than the compound of example 15 having a concentration of 1 pM. D represents that the compound of example 15 having a concentration of 100 pM exhibits the strongest effect, the ganglion processes are obviously longer and denser than that of A, B and C.

Example 56

The neurotrophic activity of the compounds of the present invention can also be determined in several animal pharmacological models in vivo, such as the model of adult mice sympathetic nerve endings damaged by 6-hydroxy-dopamine (6-OHDA).

Kunming species female mice (□) having a body weight of 18-22 g are randomly divided into the following groups: normal control group, model control group, FK506 (2 mg/kg) group, and the group of compound of the present invention (10 mg/kg) (10 mice per group). The mice are administrated with 6-OHDA (8 mg/kg) by intraperitoneal injection before 4 hours and after 4 continuous days of subcutaneous injection of the compound, while the control groups are administrated with the equivalent quantity of carrier by subcutaneous injection. After two weeks of the last administration, the mice are killed by luxation, and the two submaxillary glands of each of the mice are rapidly excised and weighed, placed in a glass grinder, then is homogenated with a homogenating liquid containing internal-standard, and centrifuged at 2000 g for 30 minutes. 20 µL of the obtained supernatant is directly injected in an HPLC-electrochemical detector to measure the content of noradrenaline (NE) in the submaxillary glands of the mice. The results are shown in FIG. 2.

Figure 2:
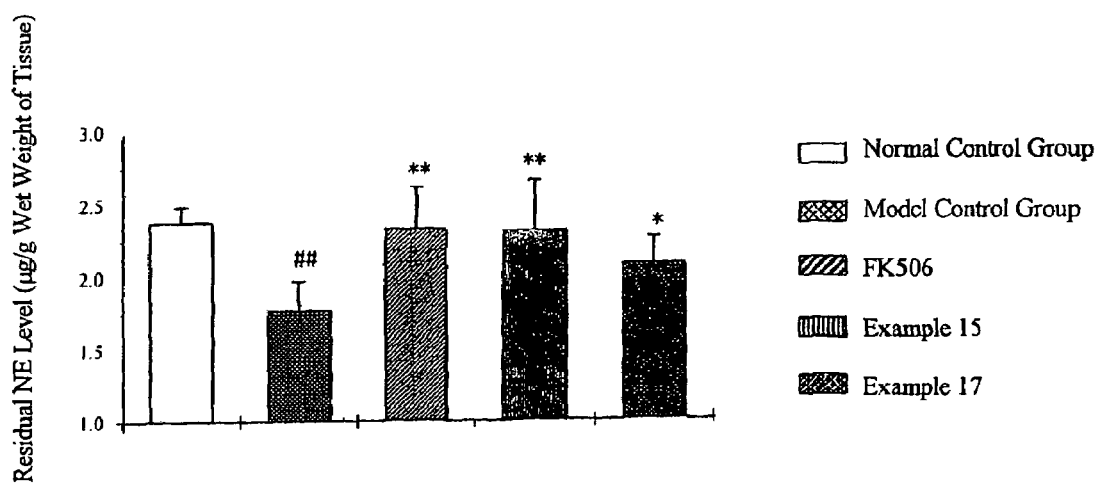

FIG. 2 indicates the effect of the representative compounds of the Examples 15 and 17 on the level of residual NE in the submaxillary glands of the mice whose sympathetic nerve terminals are damaged with 6-OHDA. It can be seen that after the administration of 6-OHDA (8 mg/kg) by intraperitoneal injection, the content of the residual NE in the submaxillary glands of the mice decreases significantly, and the P<0.01 in comparison with the normal group. The compounds of examples 15 and 17 (10 mg/kg) raise the residual NE level in the submaxillary glands of the mice, and alleviate the damage of 6-OHDA to the sympathetic nerve terminal endings. (##P<0.01 vs normal control group, *P< 0.05 vs model control group, **P<0.01 vs model control group).

REFERENCES 1. (a) Apfer, S. C.; Arezzo, J. C.; Lipson, L.; Kesslere, J. A. Nerve growth factor prevents experimental cisplatin neuropathy. *Ann. Neurol.* 1992, 31, 76-80. (b) Apfel, S. C.; Arezzo, J. C.; Brownlee, M.; Federoff, H.; Kessler, J. A. Nerve growth factor administration protects against experimental diabetic sensory neuropathy. *Brain Res.* 1994, 634, 7-12. (c) Mcmahon, S. B.; Priestley, J. V. Peripheral neuropathies and neurotrophic factors: animal models and clinical prospectives. *Curr. Opin. Neurobiol.* 1995, 5, 616-624. (d) Martinez-Serrano, A.; Lundberg, C.; Horellou, P.; Fischer, W.; Bentlage, C.; Campbell, K.; Mckay, R. D.; Mallet, J.; Bjorklund, A. CNS-derived neural progenitor cells for gene transfer of nerve growth factor to the adult rat brain: complete rescue of axotomized cholinergic neurons after transplantation into the septum. *J. Neurosci.* 1995, 15, 5668-5680. (e) Gash, D. M.; Zhang, Z.; Ovadia, A.; Cass, W. A.; Yi, A.; Simmerman, L.; Russell, D.; Martin, D.; Lapchak, P. A.; Collins, F.; Hoffer, B. J.; Gerhardt, G. A. Functional recovery in parkinsonian monkeys treated with GDNF. *Nature* 1996, 380, 252-255.

2. Steiner, J. P.; Dawson, T. M.; Fotuhi, M.; Blue, M.; Glatt, C. E.; Snowman, A. M.; Cohen, N,; Snyder, S. H. High brain densities of the immunophilin FKBP colocalized with calcineurin. *Nature* 1992, 358, 584-587.

3. (a) Sharkey, J.; Butcher, S. P. Immunophilins mediate the neuroprotective effects of FK506 in focal cerebral ischaemia. *Nature* 1994, 371, 336-338. (b) Lyons, W. E; George, E. B.; Dawson, T. M.; Steiner, J. P.; Snyder, S. H. Immunosuppresant FK506 promotes neurite outgrowth in cultures of PC-12 cells and sensory ganglia. *Proc. Natl. Acad. Sci. USA* 1994, 91, 3191-3195. (c) Gold, B. G.; Storm-Dickerson, T.; Austin, D. R. The immunosuppressant FK506 increases functional recovery and nerve regeneration following peripheral nerve injury. *Restor. Neurol. Neurosci.* 1994, 6, 287-298. (d) Gold, B. G.; Katoh, K.; Storm-Dickerson, T. The immunosuppressant FK506 increases the rate of axonal regeneration in rat sciatic nerve. *J. Neurosci.* 1995, 15, 7509-7516. (e) Wang, M. S.; Zeleny-Pooley, M.; Gold, B. G. Comparative dose-dependence study of FK506 and cyclosporin A on the rate of axonal regeneration in rat sciatic nerve. *J. Pharmacol. Exp. Ther.* 1997, 282, 1084-1093. (f) Carreau, A.; Gueugnon, J.; Benavides, J.; Vige, X. Comparative effects of FK-506, rapamycin and cyclosporin A, on the in vitro differentiation of dorsal root ganglia explants and septal cholinergic neurons. *Neuropharmacol.* 1997, 36, 1755-1762.

4. Starzl, T. E.; Makowka, L.; Todo, S. FK-506: A potential breakthrough in immunosuppression. *Transplant Proc.* 1987, 19, S3-S 104.

5. Kopp, J. B.; Klotman, P. E. Cellular and molecular mechanisms of cyclosporin nephrotoxicity. *J. Am. Soc. Nephrol.* 1991, 1, 162-179.

6. De Groen, D. G.; Aksamit, A. J.; Rakela, J.; Forbes, G. S.; Krom, R. A. F. Central nervous system toxicity after liver transplantation. *N. Engl. J. Med.* 1987, 317, 861-866.

7. Kahan, B. D. Drug therapy: cyclosporine. *N. Engl. J. Med.* 1989, 321, 1725-1738.

8. Refouvelet, B.; Harraga, S.; Nicod, L.; Robert, J.-F.; Seilles, E.; Couquelet, J.; Tronche, P. Immunomodulatory agents: dioxothiadiazabicyclo[3.3.0]octanes and their 2-spiro derivatives. *Chem. Pharm. Bull.* 1994, 42, 1076-1083.

9. Falorni, M.; Collu, C.; Conti S.; Giacomelli, G. Chiral ligands containing heteroatoms. 14. 1,3-Oxazolidinyl methanols as chiral catalysts in the enantioselective addition of diethylzinc to aldehydes. *Thetrahedron* 1996, 7, 293-299.

What is claimed is:

1. A compound is selected from the group consisting of:
   3-(3-pyridyl)-1-propyl (2S)-5,5-dimethyl-1-(2-cyclohexyl-1,2-dioxoethyl)-2-(4-thiazolidine)carboxylate,
   3-phenyl-1-propyl (2S)-5,5-dimethyl-1-(2-cyclohexyl-1,2-dioxoethyl)-2-(4-thiazolidine)carboxylate,
   (E)-3-phenyl-prop-2-en-1-yl (2S)-5,5-dimethyl-1-(2-cyclohexyl-1,2-dioxoethyl)-2-(4-thiazolidine)carboxylate,
   3-phenoxy-1-propyl (2S)-5,5-dimethyl-1-(2-cyclohexyl-1,2-dioxoethyl)-2-(4-thiazolidine)carboxylate,
   2-[N-ethyl-N-(3-methylphenyl)]amino-1-ethyl (2S)-5,5-dimethyl-1-(2-cyclohexyl-1,2-dioxoethyl)-2-(4-thiazolidine)carboxylate,
   2-(2-thienyl)-1-ethyl (2S)-5,5-dimethyl-1-(2-cyclohexyl-1,2-dioxoethyl)-2-(4-thiazolidine)carboxylate,
   dec-9-en-1-yl (2S)-5,5-dimethyl-1-(2-cyclohexyl-1,2-dioxoethyl)-2-(4-thiazolidine)carboxylate,
   3-(3-pyridyl)-1-propyl (2S)-5,5-dimethyl-1-(2-cyclopentyl-1,2-dioxoethyl)-2-(4-thiazolidine)carboxylate,
   3-(3-pyridyl)-1-propyl (2S)-5,5-dimethyl-1-(3,3-dimethyl-1,2-dioxopentyl)-2-(4-thiazolidine)carboxylate,
   3-phenyl-1-propyl (2S)-5,5-dimethyl-1-(3,3-dimethyl-1,2-dioxopentyl)-2-(4-thiazolidine)carboxylate,
   (E)-3-phenyl-prop-2-en-1-yl (2S)-5,5-dimethyl-1-(3,3-dimethyl-1,2-dioxopentyl)-2-(4-thiazolidine)carboxylate,
   3-phenoxy-1-propyl (2S)-5,5-dimethyl-1-(3,3-dimethyl-1,2-dioxopentyl)-2-(4-thiazolidine)carboxylate,
   2-[N-ethyl-N-(3-methylphenyl)]amino-1-ethyl (2S)-5,5-dimethyl-1-(3,3-dimethyl-1,2-dioxopentyl)-2-(4-thiazolidine)carboxylate,
   2-(2-thienyl)-1-ethyl (2S)-5,5-dimethyl-1-(3,3-dimethyl-1,2-dioxopentyl)-2-(4-thiazolidine)carboxylate,
   3-(3-pyridyl)-1-propyl (2S)-5,5-dimethyl-1-(3,3-dimethyl-1,2-dioxobutyl)-2-(4-thiazolidine)carboxylate,
   3-(6-methyl-2-pyridyl)-1-propyl (2S)-5,5-dimethyl-1-(3,3-dimethyl-1,2-dioxobutyl)-2-(4-thiazolidine)carboxylate,
   3-phenyl-1-propyl (2S)-5,5-dimethyl-1-(3,3-dimethyl-1,2-dioxobutyl)-2-(4-thiazolidine)carboxylate,
   (E)-3-phenyl-prop-2-en-1-yl (2S)-5,5-dimethyl-1-(3,3-dimethyl-1,2-dioxobutyl)-2-(4-thiazolidine)carboxylate,
   1-phenoxy-2-propyl (2S)-5,5-dimethyl-1-(3,3-dimethyl-1,2-dioxobutyl)-2-(4-thiazolidine)carboxylate,
   3-cyclohexyl-1-propyl (2S)-5,5-dimethyl-1-(3,3-dimethyl-1,2-dioxobutyl)-2-(4-thiazolidine)carboxylate,
   (1R)-1-(4-methoxyphenyl)-3-phenyl-1-propyl (2S)-5,5-dimethyl-1-(3,3-dimethyl-1,2-dioxobutyl)-2-(4-thiazolidine)carboxylate,
   3-(N,N-dibenzylamino)-1-propyl (2S)-5,5-dimethyl-1-(3,3-dimethyl-1,2-dioxobutyl)-2-(4-thiazolidine)carboxylate,
   dec-9-en-1-yl (2S)-5,5-dimethyl-1-(3,3-dimethyl-1,2-dioxobutyl)-2-(4-thiazolidine)carboxylate,
   (2R)-1-methoxy-2-propyl (2S)-5,5-dimethyl-1-(3,3-dimethyl-1,2-dioxobutyl)-2-(4-thiazolidine)carboxylate,
   3-(3-pyridyl)-1-propyl (2S)-5,5-dimethyl-1-(1,2-dioxooctyl)-2-(4-thiazolidine)carboxylate,
   3-(6-methyl-2-pyridyl)-1-propyl (2S)-5,5-dimethyl-1-(1,2-dioxooctyl)-2-(4-thiazolidine)carboxylate,
   3-phenyl-1-propyl (2S)-5,5-dimethyl-1-(1,2-dioxooctyl)-2-(4-thiazolidine)carboxylate,
   (E)-3-phenyl-prop-2-en-1-yl (2S)-5,5-dimethyl-1-(1,2-dioxooctyl)-2-(4-thiazolidine)carboxylate,
   2-(2-chlorophenyl)-1-ethyl (2S)-5,5-dimethyl-1-(1,2-dioxooctyl)-2-(4-thiazolidine)carboxylate,
   3-(3-pyridyl)-1-propyl (2S)-5,5-dimethyl-1-(1,2-dioxodecyl)-2-(4-thiazolidine)carboxylate,
   3-(6-methyl-2-pyridyl)-1-propyl (2S)-5,5-dimethyl-1-(1,2-dioxodecyl)-2-(4-thiazolidine)carboxylate,
   2-(2-chlorophenyl)-1-ethyl (2S)-5,5-dimethyl-1-(1,2-dioxodecyl)-2-(4-thiazolidine)carboxylate,
   (2R)-1-methoxy-2-propyl (2S)-5,5-dimethyl-1-(1,2-dioxodecyl)-2-(4-thiazolidine)carboxylate,
   2-pentyl (2S)-5,5-dimethyl-1-(1,2-dioxodecyl)-2-(4-thiazolidine)carboxylate,
   3-(3-pyridyl)-1-propyl (2S)-5,5-dimethyl-1-(1,2-dioxo-2-phenyl)ethyl-2-(4-thiazolidine)carboxylate,
   3-phenyl-1-propyl (2S)-5,5-dimethyl-1-(1,2-dioxo-2-phenyl)ethyl-2-(4-thiazolidine)carboxylate,
   (E)-3-phenyl-prop-2-en-1-yl (2S)-5,5-dimethyl-1-(1,2-dioxo-2-phenyl)ethyl-2-(4-thiazolidine)carboxylate,
   3-cyclohexyl-1-propyl (2S)-5,5-dimethyl-1-(1,2-dioxo-2-phenyl)ethyl-2-(4-thiazolidine)carboxylate,
   dec-9-en-1-yl (2S)-5,5-dimethyl-1-(1,2-dioxo-2-phenyl)ethyl-2-(4-thiazolidine)carboxylate,
   3-(3-pyridyl)-1-propyl (2S)-5,5-dimethyl-1-[2-(4-chlorophenyl)-1,2-dioxoethyl]-2-(4-thiazolidine)carboxylate,
   3-(3-pyridyl)-1-propyl (2S)-5,5-dimethyl-1-[1,2-dioxo-2-(2,4,6-trimethylphenyl]ethyl-2-(4-thiazolidine)carboxylate,
   3-phenyl-1-propyl (2S)-5,5-dimethyl-1-[1,2-dioxo-2-(2,4,6-trimethylphenyl)]ethyl-2-(4-thiazolidine)carboxylate,
   (E)-3-phenyl-prop-2-en-1-yl (2S)-5,5-dimethyl-1-[1,2-dioxo-2-(2,4,6-trimethylphenyl)]ethyl-2-(4-thiazolidine)carboxylate,
   3-cyclohexyl-1-propyl (2S)-5,5-dimethyl-1-[1,2-dioxo-2-(2,4,6-trimethylphenyl)]ethyl-2-(4-thiazolidine)carboxylate,
   3-phenoxy-1-propyl (2S)-5,5-dimethyl-1-[1,2-dioxo-2-(2,4,6-trimethylphenyl)]ethyl-2-(4-thiazolidine)carboxylate,
   2-(2-thienyl)-1-ethyl (2S)-5,5-dimethyl-1-[1,2-dioxo-2-(2,4,6-trimethylphenyl)]ethyl-2-(4-thiazolidine)carboxylate,
   2-aminobenzyl (2S)-5,5-dimethyl-1-[1,2-dioxo-2-(2,4,6-trimethylphenyl)]ethyl-2-(4-thiazolidine)carboxylate,
   2-(N-benzyl-N-methyl)amino-1-ethyl (2S)-5,5-dimethyl-1-[1,2-dioxo-2-(2,4,6-trimethylphenyl)]ethyl-2-(4-thiazolidine)carboxylate, 1-phenoxy-2-propyl (2S)-5,5-dimethyl-1-[1,2-dioxo-2-(2,4,6-trimethylphenyl)]ethyl-2-(4-thiazolidine)carboxylate, dec-9-en-1-yl (2S)-5,5-dimethyl-1-[1,2-dioxo-2-(2,4,6-trimethylphenyl)]ethyl-2-(4-thiazolidine)carboxylate, 3-(3-pyridyl)-1-propyl (2S)-5,5-dimethyl-1-(1,2-dioxo-4-methyl-4-phenyl)pentyl-2-(4-thiazolidine)carboxylate, and 2-phenylbenzyl (2S)-5,5-dimethyl-1-(1,2-dioxo-4-methyl-4-phenyl)pentyl-2-(4-thiazolidine)carboxylate, or a pharmaceutically acceptable salt or a hydrate thereof.

2. A compound according to claim 1, wherein said compound is selected from a group consisting of:

3-(3-pyridyl)-1-propyl (2S)-5,5-dimethyl-1-(3,3-dimethyl-1,2-dioxobutyl)-2-(4-thiazolidine)carboxylate, and 3-phenyl-1-propyl (2S)-5,5-dimethyl-1-(3,3-dimethyl-1,2-dioxobutyl)-2-(4-thiazolidine)carboxylate.

3. A pharmaceutical composition comprising of a compound according to claim 1 or claim 2 and pharmaceutically acceptable carrier.

* * * * *